(12) United States Patent
Oaks et al.

(10) Patent No.: US 8,544,330 B2
(45) Date of Patent: Oct. 1, 2013

(54) METHOD AND SYSTEM FOR COOLING AN ULTRASOUND PROBE

(75) Inventors: David Oaks, Sammamish, WA (US); Chris Sanders, Redmond, WA (US)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 286 days.

(21) Appl. No.: 12/878,567

(22) Filed: Sep. 9, 2010

(65) Prior Publication Data
US 2012/0060610 A1    Mar. 15, 2012

(51) Int. Cl.
*G01N 29/00*    (2006.01)
*A61B 8/00*    (2006.01)

(52) U.S. Cl.
USPC .............................................. 73/632; 600/459

(58) Field of Classification Search
USPC .................. 73/632, 618, 626; 600/437, 443, 600/459
See application file for complete search history.

(56) References Cited

U.S. PATENT DOCUMENTS

| | | | | |
|---|---|---|---|---|
| 5,961,465 A | * | 10/1999 | Kelly et al. | 600/459 |
| 6,106,148 A | * | 8/2000 | Moslehi et al. | 374/1 |
| 7,052,463 B2 | | 5/2006 | Peszynski et al. | |
| 7,314,447 B2 | * | 1/2008 | Park et al. | 600/459 |
| 7,891,230 B2 | * | 2/2011 | Randall | 73/1.82 |
| 7,918,799 B2 | * | 4/2011 | Haveri | 600/459 |
| 2004/0002655 A1 | | 1/2004 | Bolorforosh et al. | |
| 2004/0059226 A1 | | 3/2004 | Peszynski et al. | |
| 2005/0075573 A1 | | 4/2005 | Park et al. | |
| 2005/0215892 A1 | | 9/2005 | Emery et al. | |
| 2006/0100513 A1 | | 5/2006 | Hashimoto | |
| 2006/0173344 A1 | | 8/2006 | Marian et al. | |
| 2008/0188755 A1 | | 8/2008 | Hart | |

FOREIGN PATENT DOCUMENTS

| | | |
|---|---|---|
| JP | 3061292 U | 6/1999 |
| JP | 2004-113789 A | 4/2004 |
| JP | 2008-284003 A | 11/2008 |

* cited by examiner

*Primary Examiner* — J M Saint Surin
(74) *Attorney, Agent, or Firm* — Yoshida & Associates, LLC

(57) ABSTRACT

The embodiments of the probe or the probe handle additionally include an integrally formed cooling structure with at least one dividing wall that is connected to an outer wall and an inner wall of the probe. The outer wall and the inner wall of the probe together form a medium flow space inside the probe, and the dividing wall divides the medium flow space into a continuous medium flow path where a predetermined medium travels to carry undesirable heat away from the probe handle. The undesirable heat is generated from electronic components and or an array of transducer elements in the probe handle.

52 Claims, 24 Drawing Sheets

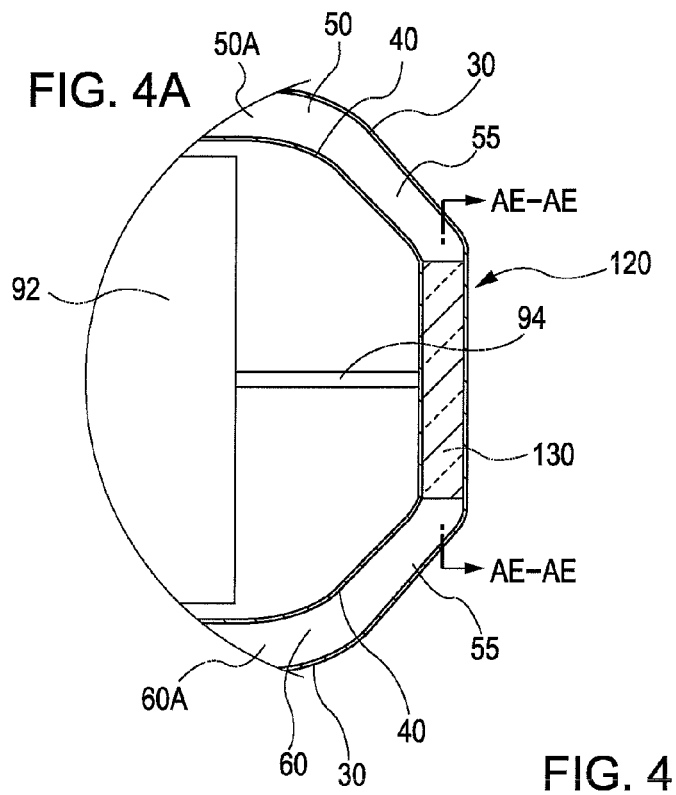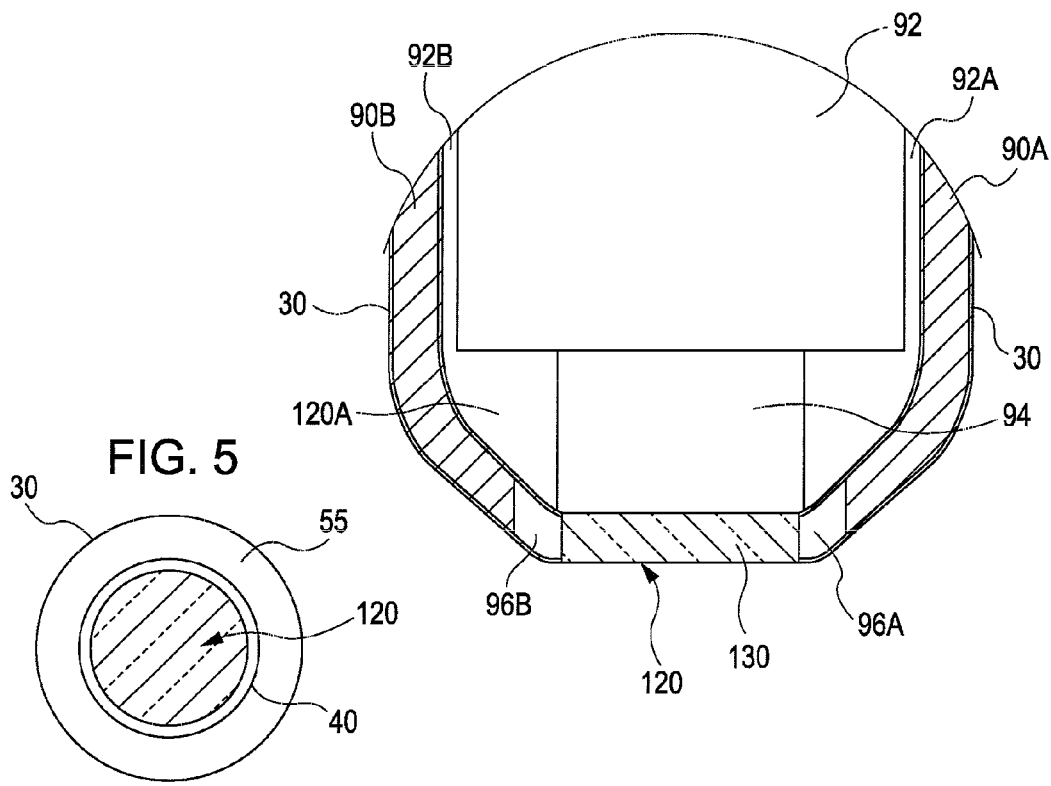

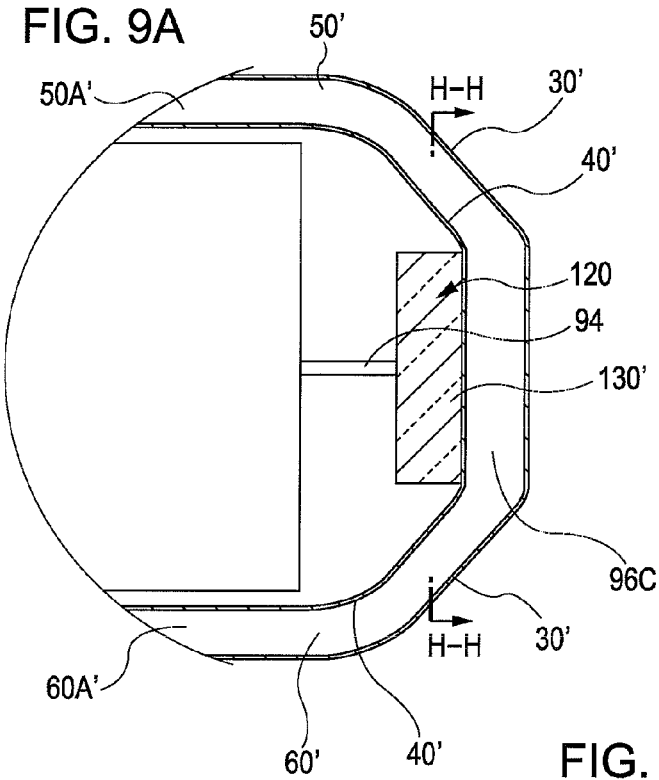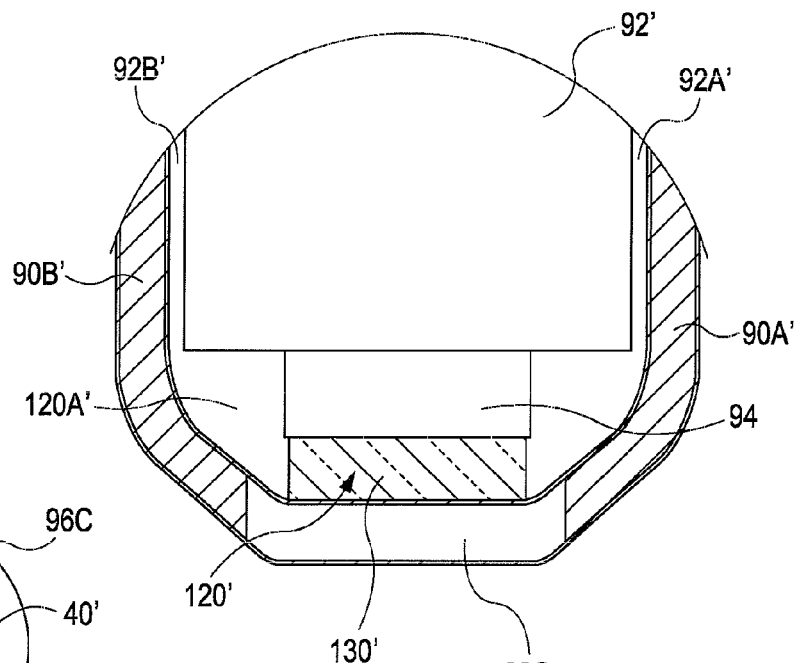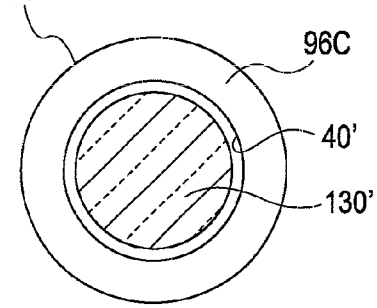

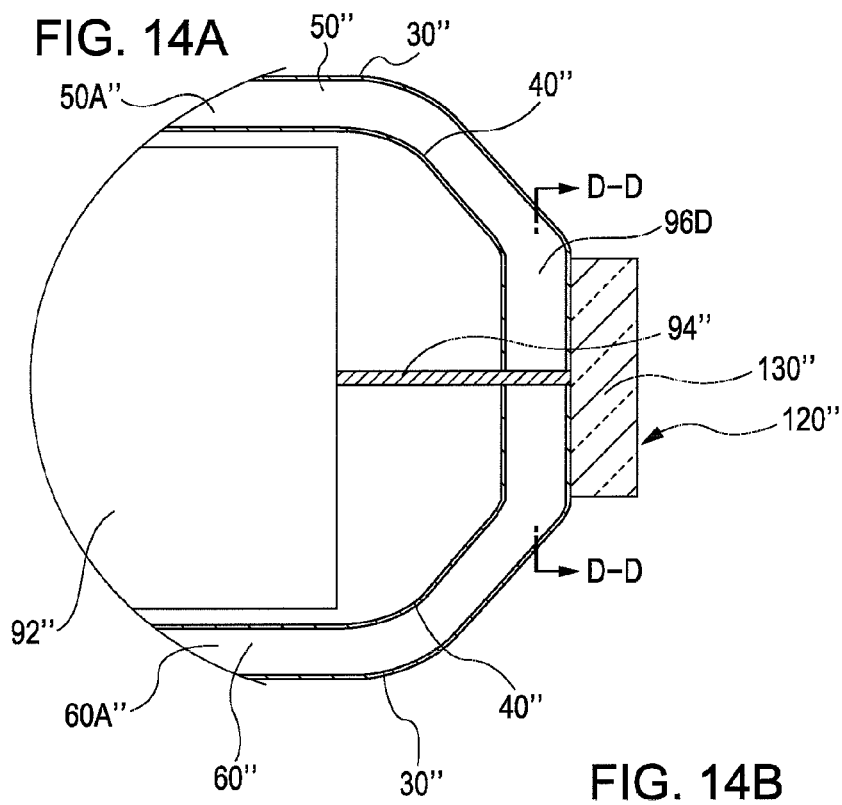
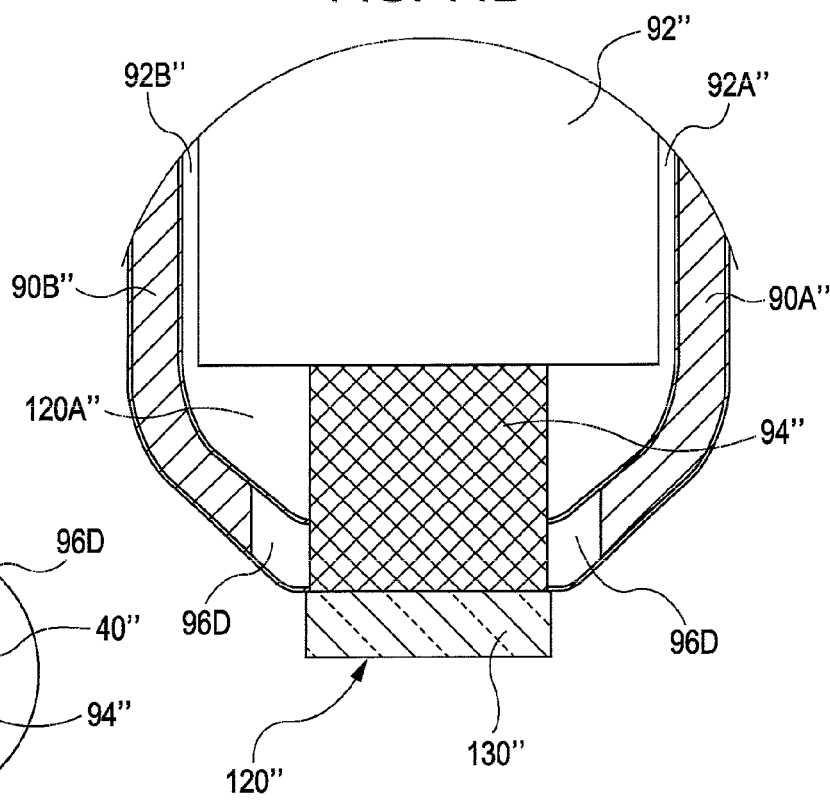
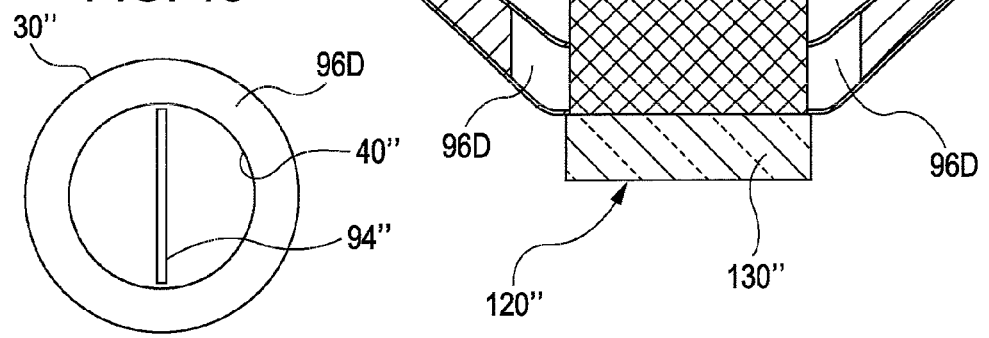

METHOD AND SYSTEM FOR COOLING AN ULTRASOUND PROBE

Embodiments described herein generally relate to an ultrasound probe and method of operating and fabricating the same.

BACKGROUND

As illustrated in FIG. 32, a conventional ultrasound imaging system includes a processing unit 1, a display unit 2, a cable 3 and a transducer unit or ultrasound probe 4.

The probe 4 is connected to the processing unit 1 via the cable 3. The processing unit 1 generally controls the transducer unit 4 for transmitting ultrasound pulses towards a region of interest in a patient and receiving the ultrasound pulses reflected from the patient. The processing unit 1 concurrently receives in real time the reflected ultrasound signals for further processing so as to display on the display unit 2 an image of the region of the interest.

In detail, the probe 4 further includes a predetermined number of transducer elements, which are grouped into channels for transmitting and receiving the ultrasound pulses. For 2-dimensional (2D) imaging data, a number of channels ranges from 64 to 256.

On the other hand, for 3-dimensional (3D) imaging data, a number of required channels often exceeds 1000's. In the above described conventional ultrasound imaging system, the probe 4 also houses a large number of electric elements such as circuits and other components for controlling the transmission and reception of the ultrasound pulses.

The above described electric elements undesirably generate wasteful heat in the probe. Because the wasteful heat conducts through the probe housing surfaces and the lens surfaces, these probe surfaces reach an undesirable or even harmful temperature during the operation of the ultrasound imaging system. For example, while an ultrasound technician holds the probe handle, the undesirable heat may cause his or her hand to sweat or burn. Consequently, not only the comfort and safety levels are decreased during the operation, but also the accuracy may be also affected due to the slippery holding surface. The undesirable heat also may affect a patient as the lens surfaces or other probe surfaces make contact on the patient's skin. As the wasteful heat reaches a certain level, the probe contacting surfaces may be even harmful from some skin damage due to burning.

Some prior art techniques have attempted to improve the probe temperature control by various means. These attempts have not yet reached a desirable efficiency and implementation.

BRIEF DESCRIPTION OF THE DRAWINGS

FIG. 4A is a diagram illustrating an enlarged cross sectional view of the first embodiment in a region Z of FIG. 2A.

FIG. 4B is a diagram illustrating an enlarged cross sectional view of the first embodiment in a region A of FIG. 2B.

FIG. 5 is a diagram illustrating of the first embodiment of the probe in a transverse cross sectional view at a predetermined plane AE-AE of FIG. 1A.

FIG. 9A is a diagram illustrating an enlarged cross sectional view of the second embodiment in a region J of FIG. 7A.

FIG. 9B is a diagram illustrating an enlarged cross sectional view of the second embodiment in a region K of FIG. 7B.

FIG. 10 is a diagram illustrating of the second embodiment of the probe in a transverse cross sectional view at a predetermined plane H-H of FIG. 6A.

FIG. 14A is a diagram illustrating an enlarged cross sectional view of the third embodiment in a region J of FIG. 12A.

FIG. 14B is a diagram illustrating an enlarged cross sectional view of the third embodiment in a region M of FIG. 12B.

FIG. 15 is a diagram illustrating of the third embodiment of the probe in a transverse cross sectional view at a predetermined plane D-D of FIG. 11A.

DETAILED DESCRIPTION

Embodiments of the ultrasound imaging system according to the current invention include a probe, a transducer unit, a processing unit and a cable connecting the probe to the processing unit. In the current application, the term, probe is interchangeably used with a probe handle. In general, the embodiments of the probe include structures, components and elements of a conventional ultrasound probe. That is, embodiments of the probe generate ultrasound pulses and transmit them towards a certain area of a patient. The embodiments also receive the ultrasound echoes reflected from the patient in order to provide an internal image of the patient. While many embodiments of the probe are generally handheld devices, some are not hand-held devices. In any case, the embodiments of the probe include a cooling structure or jacket that is integrally formed with the probe housing for promoting the cooling efficiency in removing undesirably generated heat from the probe.

Figure 1A:
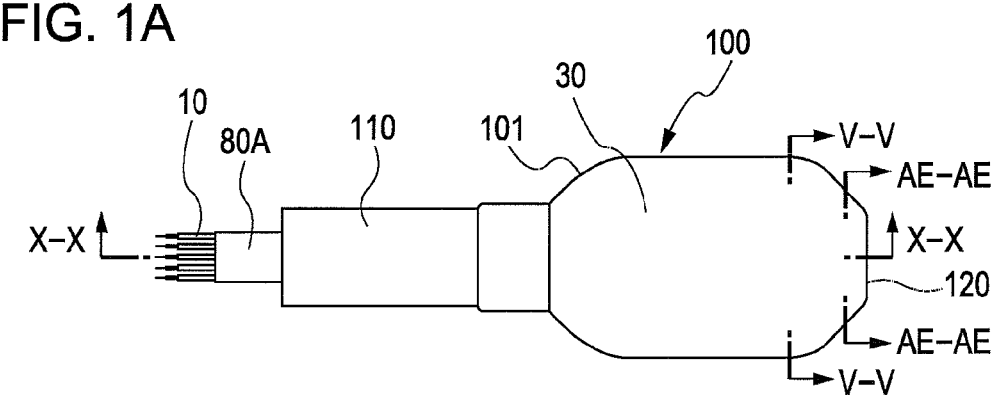
FIG. 1A is a side view illustrating a first embodiment of the probe according to the current invention.

Referring now to the drawings, wherein like reference numerals designate corresponding structures throughout the views, and referring in particular to FIG. 1A, a drawing in a side view illustrates a first embodiment of a probe according to the current invention. A probe 100 generally includes a hand holding portion or a housing portion 101 that is attached to a transducer cable 110 at one end while an array of transducer elements 120 is located at the other end. The transducer cable 110 is ultimately connected to a processing unit or a system for transmitting electrical signals via signal coax 10 to and from the probe 100. The housing portion 101 contains electronic units or components and also provides an operator with a handle area for holding the probe 100 in order to place the array 120 of the probe 100 over a desired area of a patient. As will be seen in other cross sectional views, a majority of the housing portion 101 also overlaps an outer jacket or outer wall 30 of the probe 100. Although this embodiment of the probe 100 is illustrated as a hand-held device that is cabled to the system, the claimed invention is not necessary limited by these requirements.

Figure 2A:
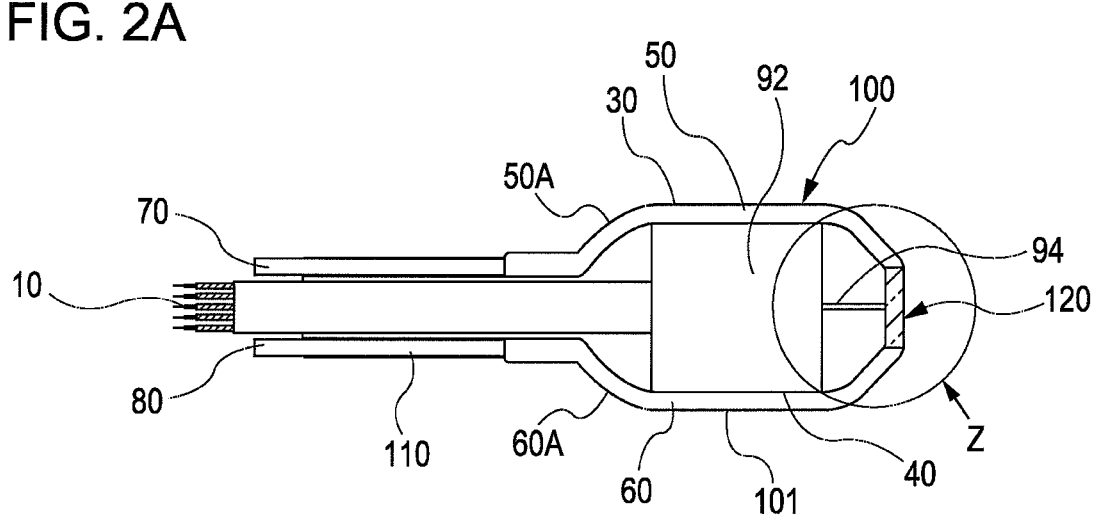
FIG. 2A is a diagram illustrating the first embodiment of the probe according to the current invention in a longitudinal cross sectional view at a predetermined plane X-X of FIG. 1A.

Now referring to FIG. 2A, a drawing illustrates the first embodiment of the probe 100 according to the current invention in a longitudinal cross sectional view on a predetermined plane X-X of FIG. 1A. The longitudinal cross sectional view illustrates that the probe 100 includes the housing portion 101, the transducer cable 110 at one end and the array 120 at the other end. The housing portion 101 houses electronic units 92 such as electronic circuits, and the signal coax 10 extends to the electronic units 92 in the transducer cable 110. A ribbon of a flexible cable 94 connects the electronic units 92 to the array 120. As already described above, a majority of the housing portion 101 overlaps the outer jacket or outer wall 30 of the probe 100, and the outer jacket or outer wall 30 extends from a point near the array 120 to a point where the housing portion 101 meets the transducer cable 110. An inner jacket or inner wall 40 is located inside the outer wall 30 and between the electronic units 92 and the outer wall 30. The inner jacket or inner wall 40 also extends in a longitudinal direction from a point near the array 120 to a point where the housing portion 101 meets the transducer cable 110.

The inner wall 40 and the outer wall 30 together form a cavity or a medium flow space 50 and 60 where a predetermined heat-carrying medium such as any combination of solid, gas and or liquid materials is contained in order to transfer the undesirable or wasteful heat generated from the electronic units 92 and or the arrays 120. A phase change in the heat-carrying medium is optionally used for heat transfer. In general, the undesirable heat travels towards the outer wall 30 through the inner wall 40. In this regard, the inner wall 40 is made of material whose heat conductive characteristic is at least higher than that of the outer wall 30 so that the wasteful heat easily conducts to the predetermined heat-carrying medium but not to the outer surfaces of the outer wall 30. For example, the inner wall 40 is made of a heat conductive material such as plastics, aluminum, carbon/aluminum, copper, graphite, any other well-known heat-conductive material or a combination of the above. Since the medium flow space 50 and 60 substantially extend in a longitudinal direction of the probe 100 and contain the predetermined heat-carrying medium, a substantial amount of the undesirable heat from the electronic units 92 and or the arrays 120 is absorbed by predetermined heat-carrying medium before reaching the outer wall 30. In one exemplary embodiment of the probe 100, the heat-carrying medium travels substantially in one direction from an intake opening 70 through the intake volume 50A into the exhaust volume 60A to an exhaust opening 80. The above described medium flow movement is not necessary to practice the current invention and can be implemented in different directions or manners.

Figure 1B:
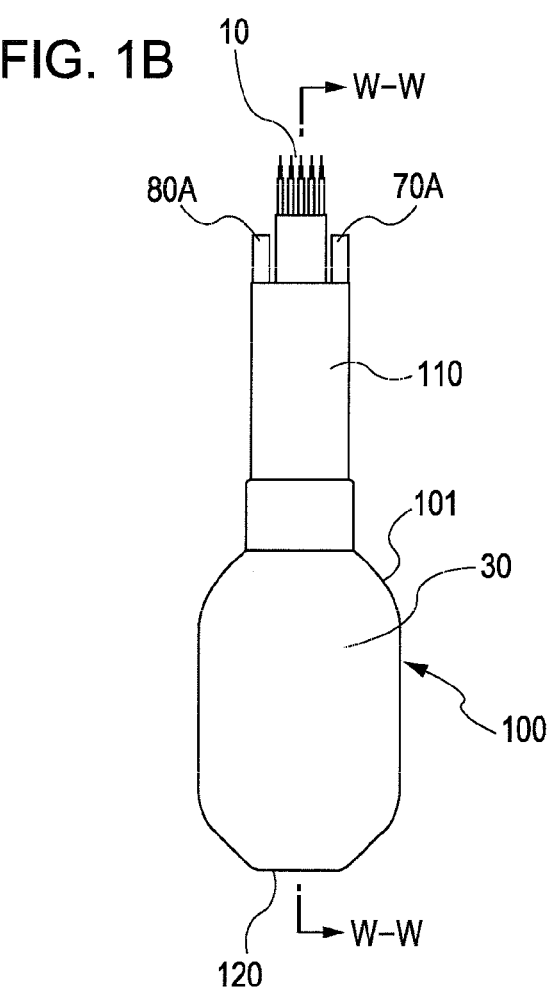
FIG. 1B is a top view illustrating a side view of the first embodiment of the probe according to the current invention.

FIG. 1B is a drawing in a top view illustrating the first embodiment of the probe according to the current invention. The top view of FIG. 1B is perpendicular to the side view of FIG. 1A. The terms, top and side views are relative and do not necessarily imply the orientation of the probe during its use. Along the longitudinal direction, one end of the hand holding portion or housing portion 101 is connected to the transducer cable 110 while the other end houses the array 120. The transducer cable 110 further includes the signal coax 10, an intake inlet 70A and an exhaust outlet 80A, and at least a pair of the tube-like inlets 70A and 80A is both located between the outer covering of the transducer cable 110 and the signal coax 10. The housing portion 101 contains the electronic units.

Figure 2B:
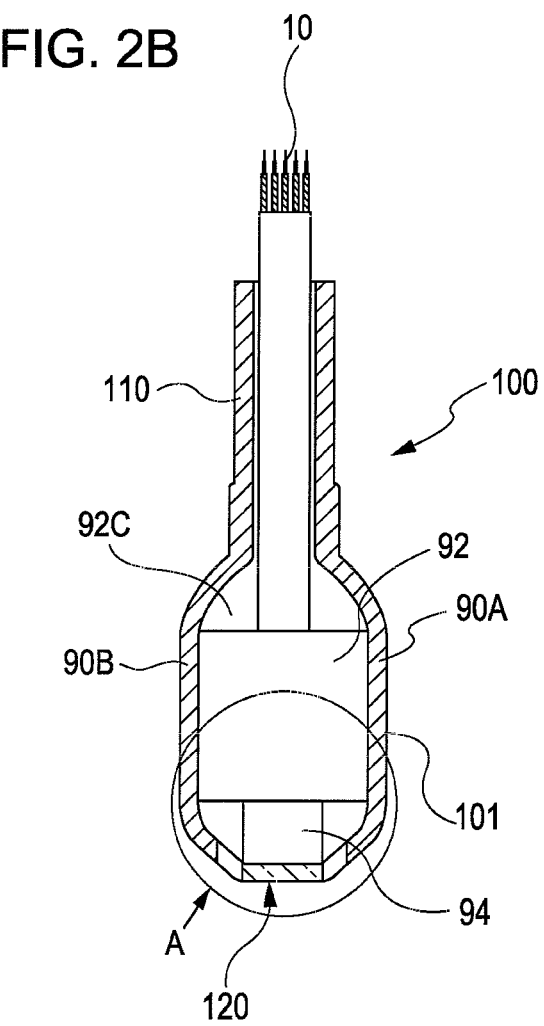
FIG. 2B is a diagram illustrating the first embodiment of the probe according to the current invention in a longitudinal cross sectional view at a predetermined plane W-W of FIG. 1B.

Now referring to FIG. 2B, a drawing illustrates the first embodiment of the probe 100 in a longitudinal cross sectional view on a predetermined plane W-W of FIG. 1B. The longitudinal cross sectional view of FIG. 2B is perpendicular to the longitudinal cross sectional view of FIG. 2A. FIG. 2B illustrates that the housing portion 101 houses electronic units 92, and the signal coax 10 is connected to the electronic units 92. A ribbon of the flexible cable 94 connects the electronic units 92 to the array 120. The longitudinal cross sectional view of FIG. 2B does not show the separation of the inner wall 40 and the outer wall 30 due to dividing walls 90A and 90B. However, as already described above with respect to FIG. 2A, a majority of the housing portion 101 overlaps the outer wall 30, which extends from a point near the array 120 to a point where the housing portion 101 meets the transducer cable 110. As also already described above, the inner wall 40 is located inside the outer wall 30 and between the electronic units 92 and the outer wall 30. The inner wall 40 also extends in a longitudinal direction from a point near the array 120 to a point where the housing portion 101 meets the transducer cable 110. The dividing walls 90A and 90B are formed between the outer wall 30 and the inner wall 40 on the predetermined plane W-W along the longitudinal direction.

The dividing walls 90A and 90B are each connected to both the inner wall 40 and the outer wall 30 and separate the medium flow space 50 and 60 into at least two halves where the predetermined heat-carrying medium such as any combination of gas and or liquid materials is contained in order to transfer the undesirable or wasteful heat generated from the electronic units 92 and or the arrays 120. The dividing walls 90A and 90B also substantially extend in a longitudinal direction from a point near the array 120 to a point where the housing portion 101 meets the transducer cable 110 as will be further explained with respect to FIGS. 4A and 4B. Since the medium flow space 50 and 60 substantially extend in the longitudinal direction of the probe 100, each of the divided medium flow spaces 50 and 60 also extends to substantially the same extent in the longitudinal direction.

Figure 3:
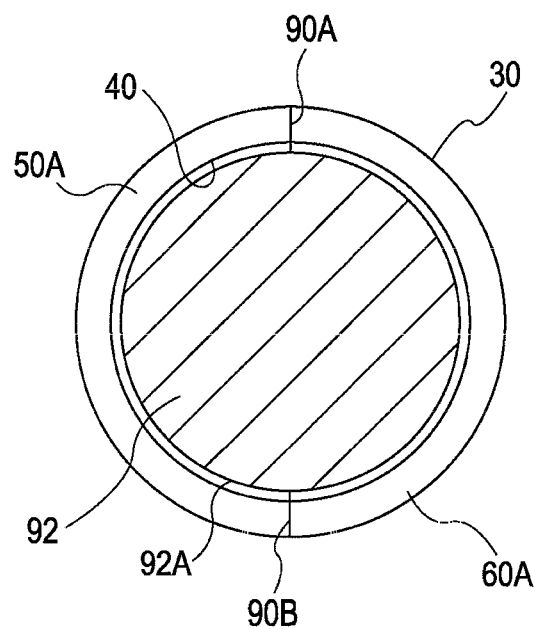
FIG. 3 is a diagram illustrating of the first embodiment of the probe in a transverse cross sectional view at a predetermined plane V-V of FIG. 1A.

Now referring to FIG. 3, the above described dividing walls 90A and 90B are illustrated in a transverse cross sectional view on a predetermined plane V-V of FIG. 1A. Both the outer wall 30 and the inner wall 40 substantially surround the heat-generating electronic units 92. The dividing walls 90A and 90B are each located between the outer wall 30 and the inner wall 40 and also each connected to both the outer wall 30 and the inner wall 40. Thus, the dividing walls 90A and 90B separate the medium flow spaces 50 and 60 into an intake volume 50A and an exhaust volume 60A. The terms, intake and exhaust do not necessarily dictate a direction of the medium flow movement, which is not necessary to practice the current invention and can be implemented in different directions or manners.

In further detail of the medium flow spaces 50 and 60, FIG. 4A illustrates an enlarged cross sectional view of the first embodiment in a region Z of FIG. 2A. The expanded cross sectional view of the region Z shows that the inner wall 40 and the outer wall 30 together form the medium flow spaces 50 and 60, which extend beyond the electronic units 92 and both abut on the side surface of the array unit 120 at the anterior end of the probe 100. The array unit 120 is covered by a lens 130 over its front end surface and is connected to the electronic units 92 via the flexible cable 94 at the rear end.

Similarly, in further detail of the dividing walls 90A and 90B, FIG. 4B illustrates an enlarged cross sectional view of the first embodiment in a region A of FIG. 2B. The expanded cross sectional view of the region A is perpendicular to the expanded cross sectional view of the region Z of FIG. 4A. For this reason, the expanded cross sectional view of the region A shows that the dividing walls 90A and 90B respectively divide a substantial portion of the medium flow space .50 and 60. By the same token, the flexible cable 94 is a ribbon-like structure, which is shown respectively as a rectangular structure in FIG. 4B and a line in FIG. 4A. As already described, the array unit 120 is covered by a lens 130 over the front end and is connected to the electronic unit 92 via the flexible cable 94 at the rear end.

Now referring to both FIGS. 4A and 4B, the dividing walls 90A and 90B extend beyond the electronic unit 92 but stop before abutting on the side surface of the array unit 120 at the anterior end of the probe 100. By this way, the dividing walls 90A and 90B respectively form pass through openings 96A and 96B near the array unit 120. The pass through openings 96A and 96B provide a connection passage between the intake volume 50A and the exhaust volume 60A in the medium flow spaces 50 and 60. The connected intake and exhaust volume 50A and 60A together form a continuous medium flow path for the predetermined medium to circulate as the predetermined medium absorbs the wasteful heat from the electronic units 92 and or the array unit 120. The flow in the continuous medium flow path is not necessarily in a single direction to practice the claimed invention. Furthermore, the number, size and location of the pass through openings 96A and 96B are optionally modified in alternative embodiments to practice the claimed invention. The continuous medium flow path is either open or closed to the environment. In addition, the circulation or flow is optionally promoted by an external device that is connected to the ports 70A and 80A in alternative embodiments.

Referring to FIG. 5, the above described pass through openings 96A and 96B are also illustrated in a transverse cross sectional view on a predetermined plane AE-AE of FIG. 1A or 4A. The transverse cross sectional view shows that the pass through openings 96A and 96B are connected to each other and form a ring-like space or pass through volume 55 around and near the array unit 120 in this exemplary embodiment. In other words, the continuous medium flow path includes at least the intake volume 50A, the pass through volume 55 and exhaust volume 60A, which are all connected together and contains the predetermined medium to circular as the wasteful heat is absorbed from the electronic unit 92 and or the array unit 120. The flow in the continuous medium flow path is not necessarily dictated by a single direction to practice the claimed invention.

Figure 6A:
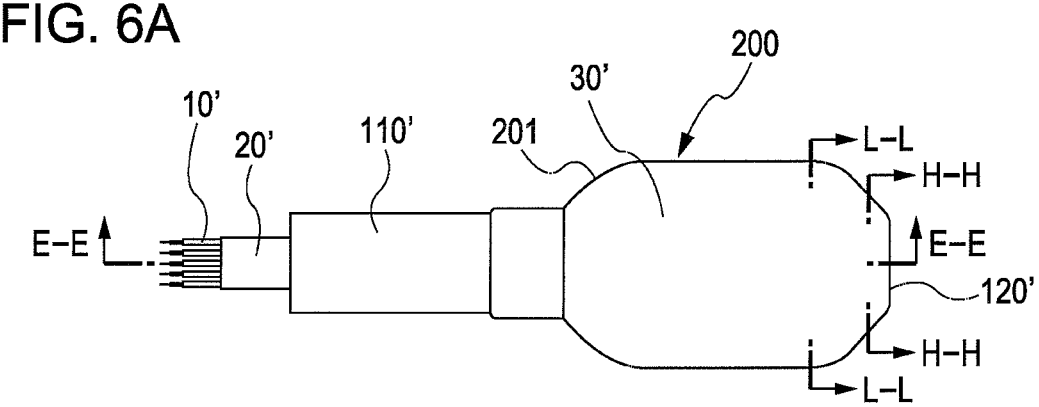
FIG. 6A is a side view illustrating a second embodiment of the probe according to the current invention.

FIG. 6A, a drawing in a side view illustrates a second embodiment of a probe according to the current invention. A probe 200 generally includes a hand holding portion or a housing portion 201 that is attached to a transducer cable 110' at one end while an array of transducer elements 120' is located at the other end. The transducer cable 110' is ultimately connected to a processing unit or a system for transmitting electrical signals via signal coax 10' to and from the probe 200. The housing portion 201 contains electronic units or components and also provides an operator with a handle area for holding the probe 200 in order to place the array 120' of the probe 200 over a desired area of a patient. As will be seen in other cross sectional views, a majority of the housing portion 201 also overlaps an outer jacket or outer wall 30' of the probe 200. Although this embodiment of the probe 200 is illustrated as a hand-held device that is cabled to the system, the claimed invention is not necessary limited by these requirements.

Figure 7A:
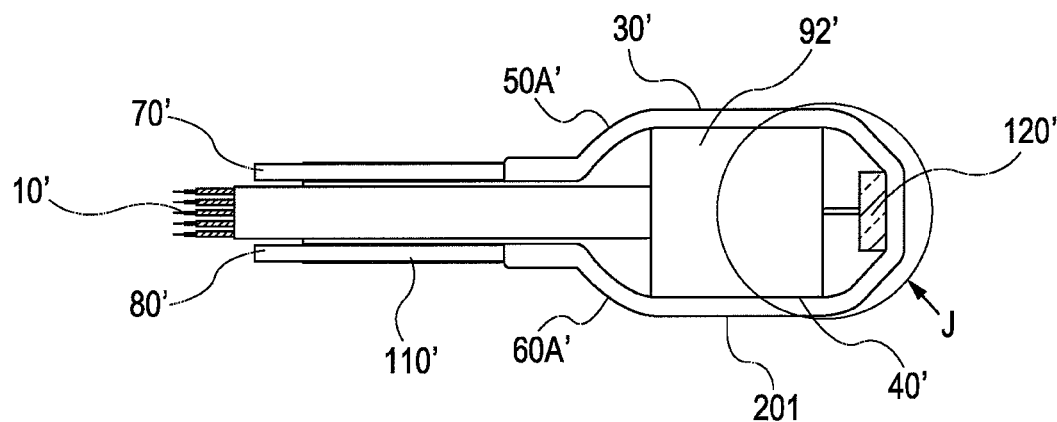
FIG. 7A is a diagram illustrating the second embodiment of the probe according to the current invention in a longitudinal cross sectional view at a predetermined plane EE-EE of FIG. 6A.

Now referring to FIG. 7A, a drawing illustrates the second embodiment of the probe 200 according to the current invention in a longitudinal cross sectional view on a predetermined plane E-E of FIG. 6A. The longitudinal cross sectional view illustrates that the probe 200 includes the housing portion 201, the transducer cable 110' at one end and the array 120' at the other end. The housing portion 201 houses electronic units 92' such as electronic circuits, and the signal coax 10' extends to the electronic units 92' in the transducer cable 110'. A ribbon of a flexible cable 94' connects the electronic units 92' to the array 120'. As already described above, a majority of the housing portion 201 overlaps the outer jacket or outer wall 30' of the probe 200, and the outer jacket or outer wall 30' extends from a point near the array 120' to a point where the housing portion 201 meets the transducer cable 110'. An inner jacket or inner wall 40' is located inside the outer wall 30' and between the electronic units 92' and the outer wall 30'. The inner jacket or inner wall 40' also extends in a longitudinal direction from a point near the array 120' to a point where the housing portion 201 meets the transducer cable 110'.

The inner wall 40' and the outer wall 30' together form a cavity or a medium flow space 50' and 60' where a predetermined heat-carrying medium such as any combination of solid, gas and or liquid materials is contained in order to transfer the undesirable or wasteful heat generated from the electronic units 92' and or the arrays 120'. A phase change in the heat-carrying medium is optionally used for heat transfer. In general, the undesirable heat travels towards the outer wall 30' through the inner wall 40'. In this regard, the inner wall 40' is made of material whose heat conductive characteristic is at least higher than that of the outer wall 30' so that the wasteful heat easily conducts to the predetermined heat-carrying medium but not to the outer surfaces of the outer wall 30'. For example, the inner wall 40' is made of a heat conductive material such as plastics, aluminum, carbon/aluminum, copper, graphite, any other well-known heat-conductive material or a combination of the above. Since the medium flow space 50' and 60' substantially extend in a longitudinal direction of the probe 200 and contain the predetermined heat-carrying medium, a substantial amount of the undesirable heat from the electronic units 92' and or the arrays 120' is absorbed by predetermined heat-carrying medium before reaching the outer wall 30'. In one exemplary embodiment of the probe 200, the heat-carrying medium travels substantially in one direction from an intake opening 70' through the intake volume 50A' into the exhaust volume 60A' to an exhaust opening 80'. The above described medium flow movement is not necessary to practice the current invention and can be implemented in different directions or manners.

Figure 6B:
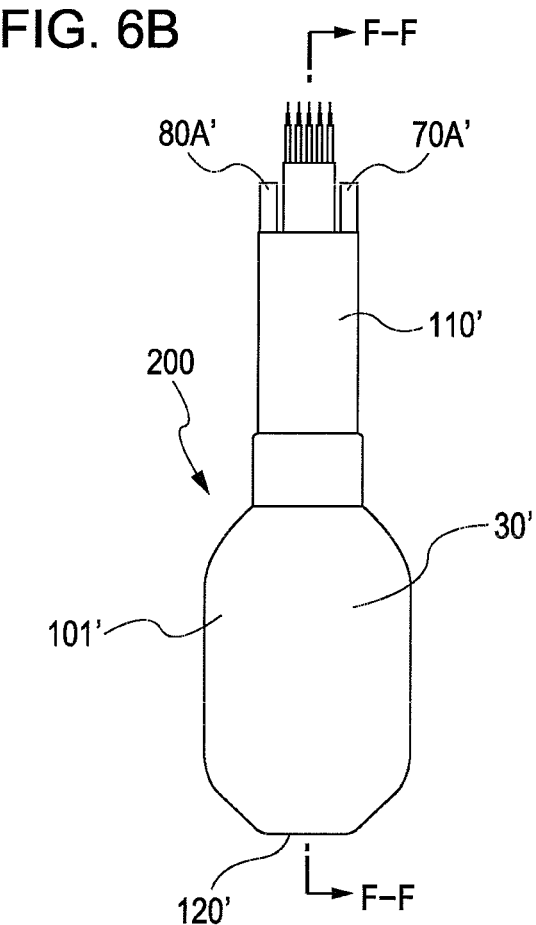
FIG. 6B is a top view illustrating a side view of the second embodiment of the probe according to the current invention.

FIG. 6B is a drawing in a top view illustrating the second embodiment of the probe according to the current invention. The top view of FIG. 6B is perpendicular to the side view of FIG. 6A. The terms, top and side views are relative and do not necessarily imply the orientation of the probe during its use. Along the longitudinal direction, one end of the hand holding portion or housing portion 201 is connected to the transducer cable 110' while the other end houses the array 120'. The transducer cable 110' further includes the signal coax 10', an intake inlet 70A' and an exhaust outlet 80A', and at least a pair of the tube-like inlets 70A' and 80A' is both located between the outer covering of the transducer cable 110' and the signal coax 10'. The housing portion 201 contains the electronic units.

Figure 7B:
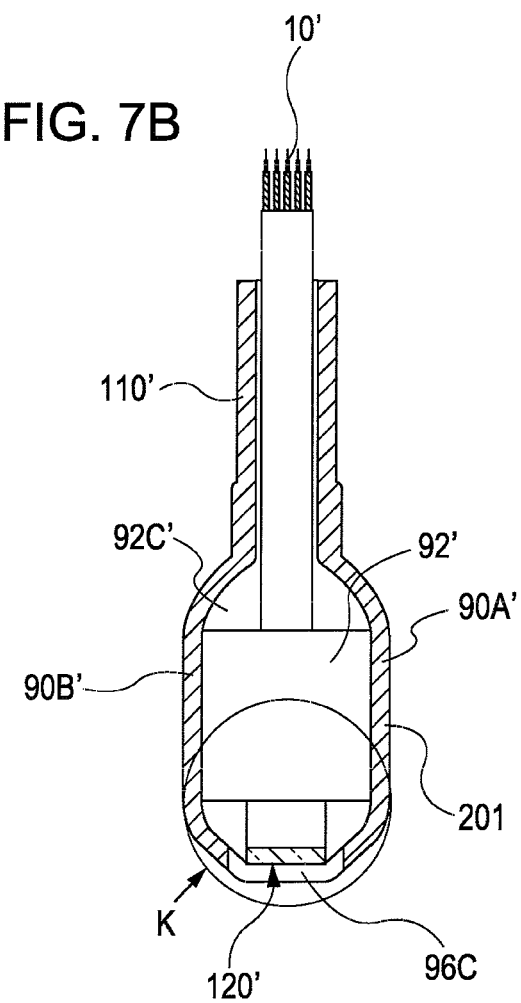
FIG. 7B is a diagram illustrating the second embodiment of the probe according to the current invention in a longitudinal cross sectional view at a predetermined plane F-F of FIG. 6B.

Now referring to FIG. 7B, a drawing illustrates the second embodiment of the probe 200 in a longitudinal cross sectional view on a predetermined plane F-F of FIG. 6B. The longitudinal cross sectional view of FIG. 7B is perpendicular to the longitudinal cross sectional view of FIG. 7A. FIG. 7B illustrates that the housing portion 201 houses electronic units 92', and the signal coax 10' is connected to the electronic units 92'.

A ribbon of the flexible cable 94' connects the electronic units 92' to the array 120'. The longitudinal cross sectional view of FIG. 7B does not show the separation of the inner wall 40' and the outer wall 30' due to dividing walls 90A' and 90B'. However, as already described above with respect to FIG. 7A, a majority of the housing portion 201 overlaps the outer wall 30', which extends from a point near the array 120' to a point where the housing portion 201 meets the transducer cable 110'. As also already described above, the inner wall 40' is located inside the outer wall 30' and between the electronic units 92' and the outer wall 30'. The inner wall 40' also extends in a longitudinal direction from a point near the array 120' to a point where the housing portion 201 meets the transducer cable 110'. The dividing walls 90A' and 90B' are formed between the outer wall 30' and the inner wall 40' on the predetermined plane F-F along the longitudinal direction.

The dividing walls 90A' and 90B' are each connected to both the inner wall 40' and the outer wall 30' and separate the medium flow space 50' and 60' into at least two halves where the predetermined heat-carrying medium such as any combination of gas and or liquid materials is contained in order to transfer the undesirable or wasteful heat generated from the electronic units 92' and or the arrays 120'. The dividing walls 90A' and 90B' also substantially extend in a longitudinal direction from a point near the array 120' to a point where the housing portion 201 meets the transducer cable 110' as will be further explained with respect to FIGS. 9A and 9B. Since the medium flow space 50' and 60' substantially extend in the longitudinal direction of the probe 200, each of the divided medium flow spaces 50' and 60' also extends to substantially the same extent in the longitudinal direction.

Figure 8:
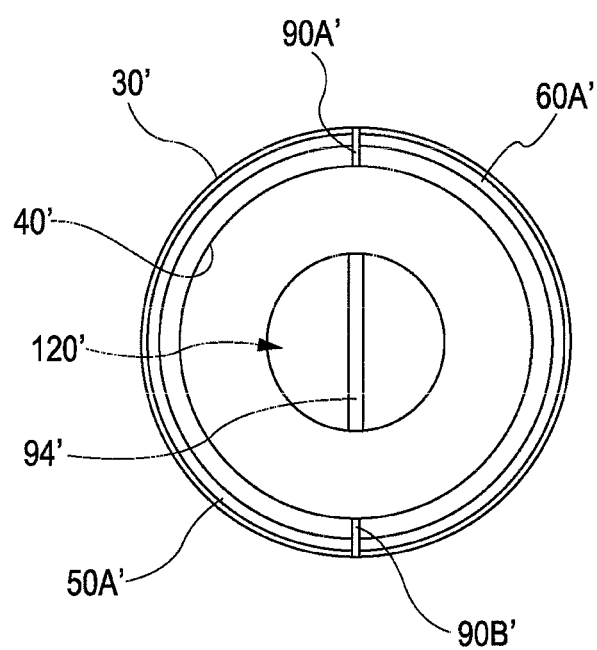
FIG. 8 is a diagram illustrating of the second embodiment of the probe in a transverse cross sectional view at a predetermined plane L-L of FIG. 6A.

Now referring to FIG. 8, the above described dividing walls 90A' and 90B' are illustrated in a transverse cross sectional view on a predetermined plane L-L of FIG. 6A. Both the outer wall 30' and the inner wall 40' substantially surround the heat-generating array 120'. The dividing walls 90A' and 90B' are each located between the outer wall 30' and the inner wall 40' and also each connected to both the outer wall 30' and the inner wall 40'. Thus, the dividing walls 90A' and 90B' separate the medium flow spaces 50' and 60' into an intake volume 50A' and an exhaust volume 60A'. The terms, intake and exhaust do not necessarily dictate a direction of the medium flow movement, which is not necessary to practice the current invention and can be implemented in different directions or manners.

In further detail of the medium flow spaces 50' and 60', FIG. 9A illustrates an enlarged cross sectional view of the second embodiment in a region J of FIG. 7A. The expanded cross sectional view of the region J shows that the inner wall 40' and the outer wall 30' together form the medium flow spaces 50' and 60', which extend beyond the electronic units 92' and in front of the array unit 120' at the anterior end of the probe 200. The array unit 120' is located behind a common pass through volume 96C, which is an extension of the medium flow spaces 50' and 60' over a front end surface of the array unit 120' while the array unit 120' is connected to the electronic units 92' via the flexible cable 94' at the rear end.

Similarly, in further detail of the dividing walls 90A' and 90B', FIG. 9B illustrates an enlarged cross sectional view of the second embodiment in a region K of FIG. 7B. The expanded cross sectional view of the region K is perpendicular to the expanded cross sectional view of the region J of FIG. 9A. For this reason, the expanded cross sectional view of the region K shows that the dividing walls 90A' and 90B' respectively divide a substantial portion of the medium flow space 50' and 60'. By the same token, the flexible cable 94' is a ribbon-like structure, which is shown respectively as a rectangular structure in FIG. 9B and a line in FIG. 9A. As already described, the array unit 120' is covered by the common pass through volume 96C over its front end surface while the array unit 120' is connected to the electronic units 92' via the flexible cable 94' at the rear end.

Now referring to both FIGS. 9A and 9B, the dividing walls 90A' and 90B' extend beyond the electronic unit 92' but stop before reaching the array unit 120' at the anterior end of the probe 200. By this way, the inner wall 40' and the outer wall 30' together form the common pass through volume 96C near and in front of the array unit 120'. The pass through volume 96C provides a connection passage between the medium flow spaces 50' and 60'. The connected intake and exhaust volume 50A' and 60A' together form a continuous medium flow path for the predetermined medium to circulate as the predetermined medium absorbs the wasteful heat from the electronic units 92' and or the array unit 120'. The flow in the continuous medium flow path is not necessarily in a single direction to practice the claimed invention. Furthermore, the number, size and location of the pass through volume 96C are optionally modified in alternative embodiments to practice the claimed invention. The continuous medium flow path is either open or closed to the environment. In addition, the circulation or flow is optionally promoted by an external device that is connected to the ports 70A' and 80A' in alternative embodiments.

Referring to FIG. 10, the above described pass through volume 96C is also illustrated in a transverse cross sectional view on a predetermined plane H-H of FIG. 6A or 9A. The transverse cross sectional view shows that the pass through volume 96C is connected to a ring-like space around and near the array unit 120' in this exemplary embodiment. In other words, the continuous medium flow path includes at least the intake volume 50A', the pass through volume 96D and exhaust volume 60A', which are all connected together and contains the predetermined medium to circular as the wasteful heat is absorbed from the electronic units 92' and or the array unit 120'. The flow in the continuous medium flow path is not necessarily dictated by a single direction to practice the claimed invention.

Figure 11A:
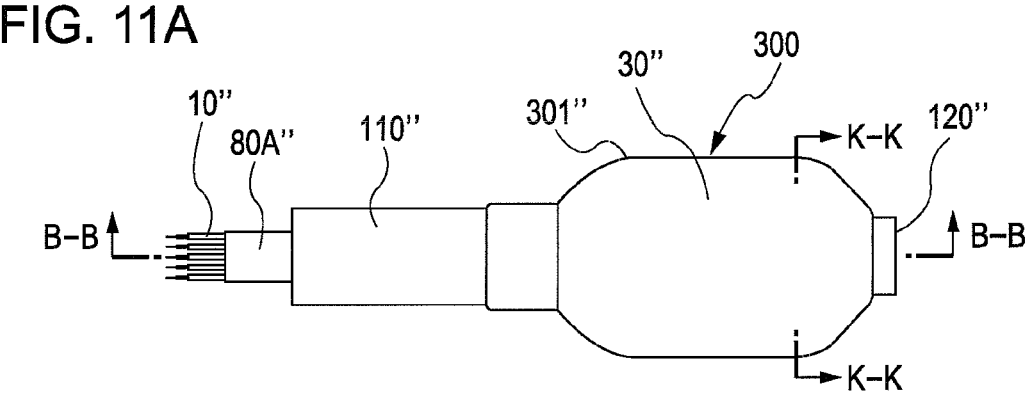
FIG. 11A is a side view illustrating a third embodiment of the probe according to the current invention.

FIG. 11A, a drawing in a side view illustrates a third embodiment of a probe according to the current invention. A probe 300 generally includes a hand holding portion or a housing portion 301 that is attached to a transducer cable 110" at one end while an array of transducer elements 120" is located at the other end. The transducer cable 110" is ultimately connected to a processing unit or a system for transmitting electrical signals via signal coax 10" to and from the probe 300. The housing portion 301 contains electronic units or components and also provides an operator with a handle area for holding the probe 300 in order to place the array 120" of the probe 300 over a desired area of a patient. As will be seen in other cross sectional views, a majority of the housing portion 301 also overlaps an outer jacket or outer wall 30" of the probe 300. Although this embodiment of the probe 300 is illustrated as a hand-held device that is cabled to the system, the claimed invention is not necessary limited by these requirements.

Figure 12A:
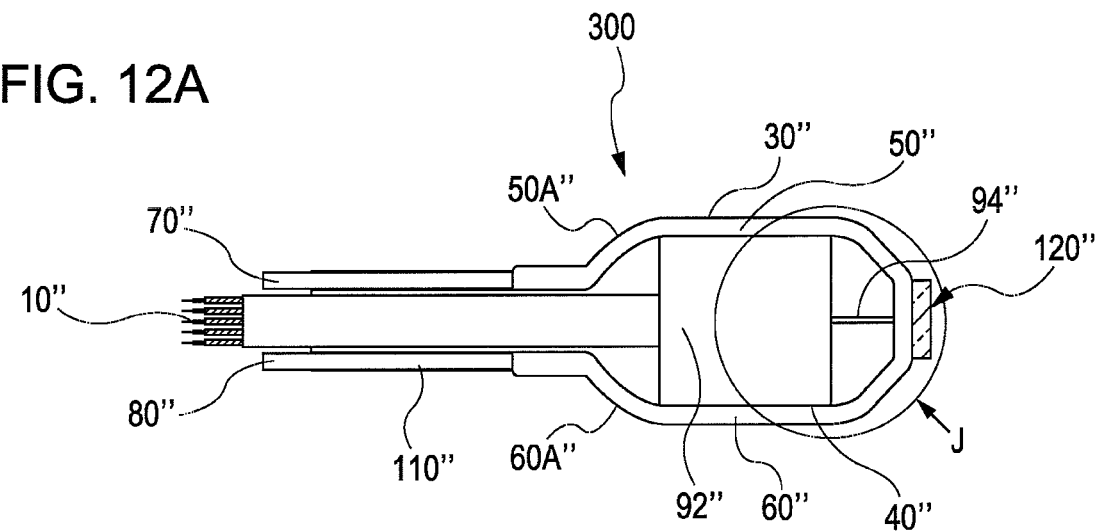
FIG. 12A is a diagram illustrating the third embodiment of the probe according to the current invention in a longitudinal cross sectional view at a predetermined plane B-B of FIG. 11A.

Now referring to FIG. 12A, a drawing illustrates the third embodiment of the probe 300 according to the current invention in a longitudinal cross sectional view on a predetermined plane B-B of FIG. 11A. The longitudinal cross sectional view illustrates that the probe 300 includes the housing portion 301, the transducer cable 110" at one end and the array 120" at the other end. The housing portion 301 houses electronic units 92", and the signal coax 10" extends to the electronic units 92" in the transducer cable 110". A ribbon of a flexible cable 94" connects the electronic units 92" to the array 120".

As already described above, a majority of the housing portion 301 overlaps the outer jacket or outer wall 30" of the probe 300, and the outer jacket or outer wall 30" extends from a point near the array 120" to a point where the housing portion 301 meets the transducer cable 110". An inner jacket or inner wall 40" is located inside the outer wall 30" and between the electronic units 92" and the outer wall 30". The inner jacket or inner wall 40" also extends in a longitudinal direction from a point near the array 120" to a point where the housing portion 301 meets the transducer cable 110".

The inner wall 40" and the outer wall 30" together form a cavity or a medium flow space 50" and 60" where a predetermined heat-carrying medium such as any combination of solid, gas and or liquid materials is contained in order to transfer the undesirable or wasteful heat generated from the electronic units 92" and or the arrays 120". A phase change in the heat-carrying medium is optionally used for heat transfer. In general, the undesirable heat travels towards the outer wall 30" through the inner wall 40". In this regard, the inner wall 40" is made of material whose heat conductive characteristic is at least higher than that of the outer wall 30" so that the wasteful heat easily conducts to the predetermined heat-carrying medium but not to the outer surfaces of the outer wall 30". For example, the inner wall 40" is made of a heat conductive material such as plastics, aluminum, carbon/aluminum, copper, graphite, any other well-known heat-conductive material or a combination of the above. Since the medium flow space 50" and 60" substantially extend in a longitudinal direction of the probe 300 and contain the predetermined heat-carrying medium, a substantial amount of the undesirable heat from the electronic units 92" and or the arrays 120" is absorbed by predetermined heat-carrying medium before reaching the outer wall 30". In one exemplary embodiment of the probe 300, the heat-carrying medium travels substantially in one direction from an intake opening 70" through the intake volume 50A" into the exhaust volume 60A" to an exhaust opening 80". The above described medium flow movement is not necessary to practice the current invention and can be implemented in different directions or manners.

Figure 11B:
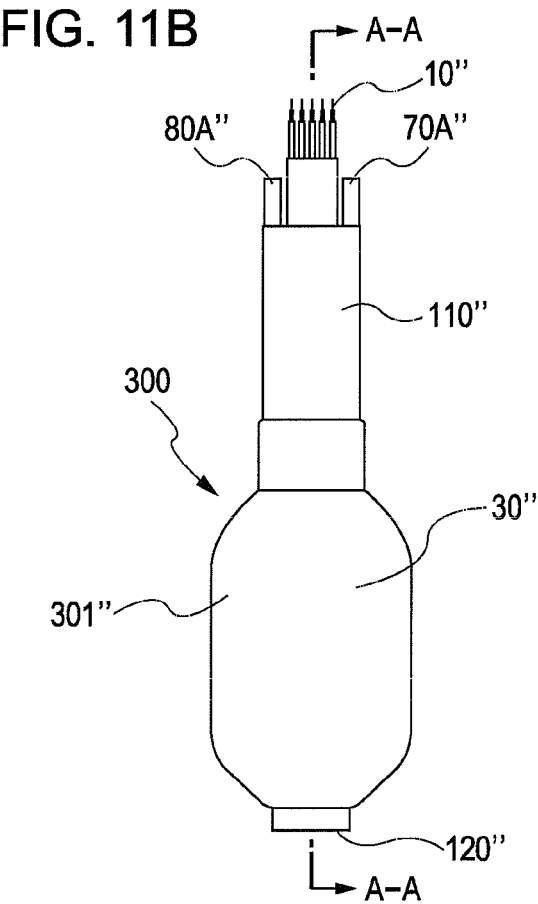
FIG. 11B is a top view illustrating a side view of the third embodiment of the probe according to the current invention.

FIG. 11B is a drawing in a top view illustrating the third embodiment of the probe according to the current invention. The top view of FIG. 11B is perpendicular to the side view of FIG. 11A. The terms, top and side views are relative and do not necessarily imply the orientation of the probe during its use. Along the longitudinal direction, one end of the hand holding portion or housing portion 301 is connected to the transducer cable 110" while the other end houses the array 120". The transducer cable 110" further includes the signal coax 10", an intake inlet 70A" and an exhaust outlet 80A", and at least a pair of the tube-like inlets 70A" and 80A" is both located between the outer covering of the transducer cable 110" and the signal coax 10". The housing portion 301 contains the electronic units.

Figure 12B:
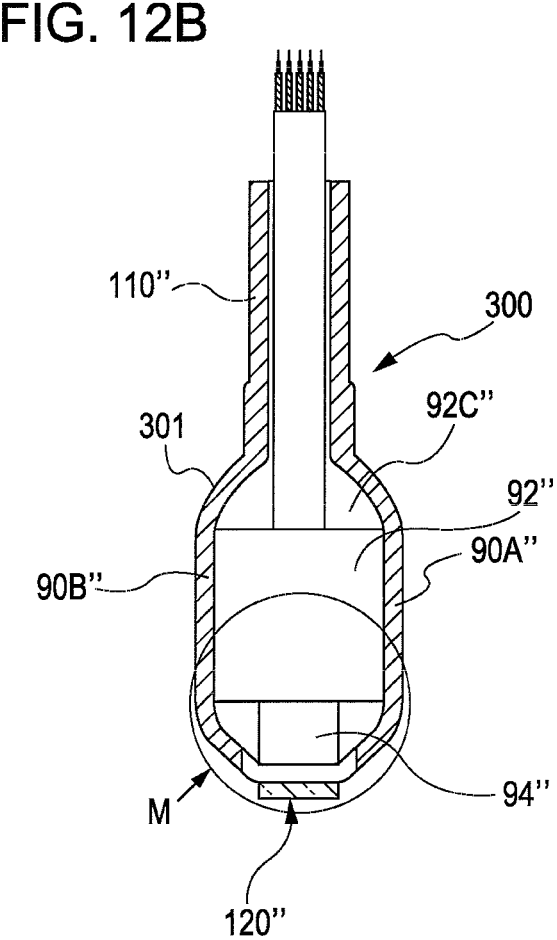
FIG. 12B is a diagram illustrating the third embodiment of the probe according to the current invention in a longitudinal cross sectional view at a predetermined plane A-A of FIG. 11B.

Now referring to FIG. 12B, a drawing illustrates the third embodiment of the probe 300 in a longitudinal cross sectional view on a predetermined plane A-A of FIG. 11B. The longitudinal cross sectional view of FIG. 12B is perpendicular to the longitudinal cross sectional view of FIG. 12A. FIG. 12B illustrates that the housing portion 301 houses electronic units 92", and the signal coax 10" is connected to the electronic units 92". A ribbon of the flexible cable 94" connects the electronic units 92" to the array 120". The longitudinal cross sectional view of FIG. 12B does not show the separation of the inner wall 40" and the outer wall 30" due to dividing walls 90A" and 90B". However, as already described above with respect to FIG. 12A, a majority of the housing portion 301 overlaps the outer wall 30", which extends from a point near the array 120" to a point where the housing portion 301 meets the transducer cable 110". As also already described above, the inner wall 40" is located inside the outer wall 30" and between the electronic units 92" and the outer wall 30". The inner wall 40" also extends in a longitudinal direction from a point near the array 120" to a point where the housing portion 301 meets the transducer cable 110". The dividing walls 90A" and 90B" are formed between the outer wall 30" and the inner wall 40" on the predetermined plane A-A along the longitudinal direction.

The dividing walls 90A" and 90B" are each connected to both the inner wall 40" and the outer wall 30" and separate the medium flow space 50" and 60" into at least two halves where the predetermined heat-carrying medium such as any combination of gas and or liquid materials is contained in order to transfer the undesirable or wasteful heat generated from the electronic units 92" and or the arrays 120". The dividing walls 90A" and 90B" also substantially extend in a longitudinal direction from a point near the array 120" to a point where the housing portion 301 meets the transducer cable 110" as will be further explained with respect to FIGS. 14A and 14B. Since the medium flow space 50" and 60" substantially extend in the longitudinal direction of the probe 300, each of the divided medium flow spaces 50" and 60" also extends to substantially the same extent in the longitudinal direction.

Figure 13:
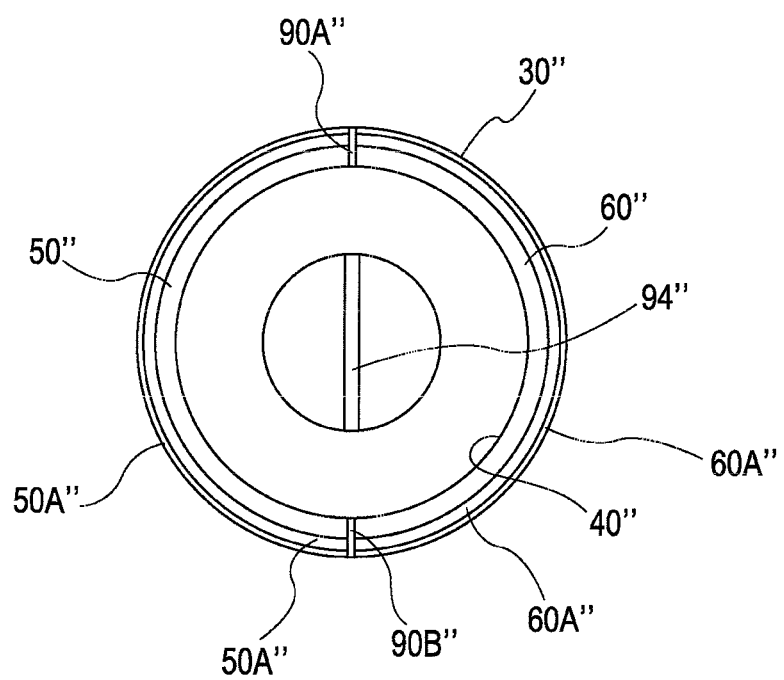
FIG. 13 is a diagram illustrating of the third embodiment of the probe in a transverse cross sectional view at a predetermined plane K-K of FIG. 11A.

Now referring to FIG. 13, the above described dividing walls 90A" and 90B" are illustrated in a transverse cross sectional view on a predetermined plane K-K of FIG. 11A. The dividing walls 90A" and 90B" are each located between the outer wall 30" and the inner wall 40" and also each connected to both the outer wall 30" and the inner wall 40". Thus, the dividing walls 90A" and 90B" separate the medium flow spaces 50" and 60" into an intake volume 50A" and an exhaust volume 60A". The terms, intake and exhaust do not necessarily dictate a direction of the medium flow movement, which is not necessary to practice the current invention and can be implemented in different directions or manners.

In further detail of the medium flow spaces 50" and 60", FIG. 14A illustrates an enlarged cross sectional view of the third embodiment in a region J of FIG. 12A. The expanded cross sectional view of the region J shows that the inner wall 40" and the outer wall 30" together form the medium flow spaces 50" and 60", which extend beyond the electronic units 92" and behind the array unit 120" at the anterior end of the probe 300.

The array unit 120" is located in front of a common pass through volume 96D, which is an extension of the medium flow spaces 50" and 60" and abuts a rear end surface of the array unit 120" while the array unit 120" is connected to the electronic units 92" via the flexible cable 94" also at the rear end.

Similarly, in further detail of the dividing walls 90A" and 90B", FIG. 14B illustrates an enlarged cross sectional view of the third embodiment in a region M of FIG. 12B. The expanded cross sectional view of the region M is perpendicular to the expanded cross sectional view of the region J of FIG. 14A. For this reason, the expanded cross sectional view of the region M shows that the dividing walls 90A" and 90B" respectively divide a substantial portion of the medium flow space 50" and 60". By the same token, the flexible cable 94" is a ribbon-like structure, which is shown respectively as a rectangular structure in FIG. 14B and a line in FIG. 14A. As already described, the array unit 120" is covered by the common pass through volume 96D over its rear end surface while the array unit 120" is connected to the electronic units 92" via the flexible cable 94" also at the rear end.

Now referring to both FIGS. 14A and 14B, the dividing walls 90A" and 90B" extend beyond the electronic unit 92" but stop before reaching the array unit 120" at the anterior end of the probe 300. By this way, the inner wall 40" and the outer wall 30" together form the common pass through volume 96D near and in front of the array unit 120". The pass through volume 96D provides a connection passage between the medium flow spaces 50" and 60". The connected intake and exhaust volume 50A" and 60A" together form a continuous medium flow path for the predetermined medium to circulate as the predetermined medium absorbs the wasteful heat from the electronic units 92" and or the array unit 120". The flow in the continuous medium flow path is not necessarily in a single direction to practice the claimed invention. Furthermore, the number, size and location of the pass through volume 96D are optionally modified in alternative embodiments to practice the claimed invention. The continuous medium flow path is either open or closed to the environment. In addition, the circulation or flow is optionally promoted by an external device that is connected to the ports 70A" and 80A" in alternative embodiments.

Referring to FIG. 15, the above described pass through volume 96D is also illustrated in a transverse cross sectional view on a predetermined plane D-D of FIG. 11A or 14A. The transverse cross sectional view shows that the pass through volume 96D is a ring-like space around and near the array unit 120" in this exemplary embodiment. In other words, the continuous medium flow path includes at least the intake volume 50A", the pass through volume 96D and exhaust volume 60A", which are all connected together and contains the predetermined medium to circular as the wasteful heat is absorbed from the electronic units 92" and or the array unit 120". The flow in the continuous medium flow path is not necessarily dictated by a single direction to practice the claimed invention.

Figure 16:
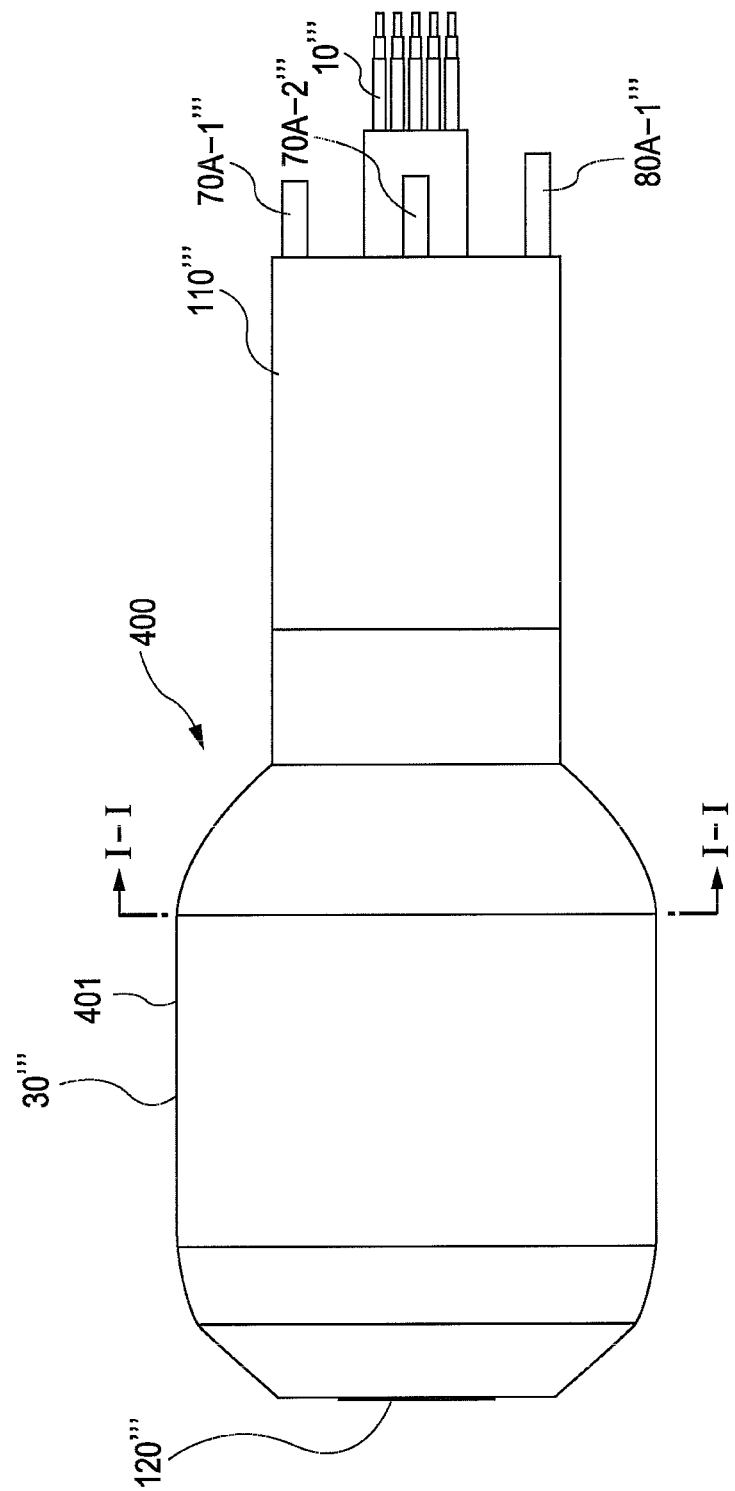
FIG. 16 is a side view illustrating a fourth embodiment of the probe according to the current invention.

FIG. 16 is a drawing in a side view illustrating a fourth embodiment of a probe according to the current invention. A probe 400 generally includes a hand holding portion or a housing portion 401 that is attached to a transducer cable 110''' at one end while an array of transducer elements 120''' is located at the other end. The transducer cable 110''' is ultimately connected to a processing unit or a system for transmitting electrical signals via signal coax 10''' to and from the probe 400. The housing portion 401 contains electronic units or components such as electronic circuits and also provides an operator with a handle area for holding the probe 400 in order to place the array 120''' of the probe 400 over a desired area of a patient. As will be seen in other cross sectional views, a majority of the housing portion 401 also overlaps an outer jacket or outer wall 30" of the probe 400. In addition, the side view also show three ports 70A-1''', 70A-2''' and 80A-1'''. Although this embodiment of the probe 400 is illustrated as a hand-held device that is cabled to the system, the claimed invention is not necessary limited by these requirements.

Figure 17:
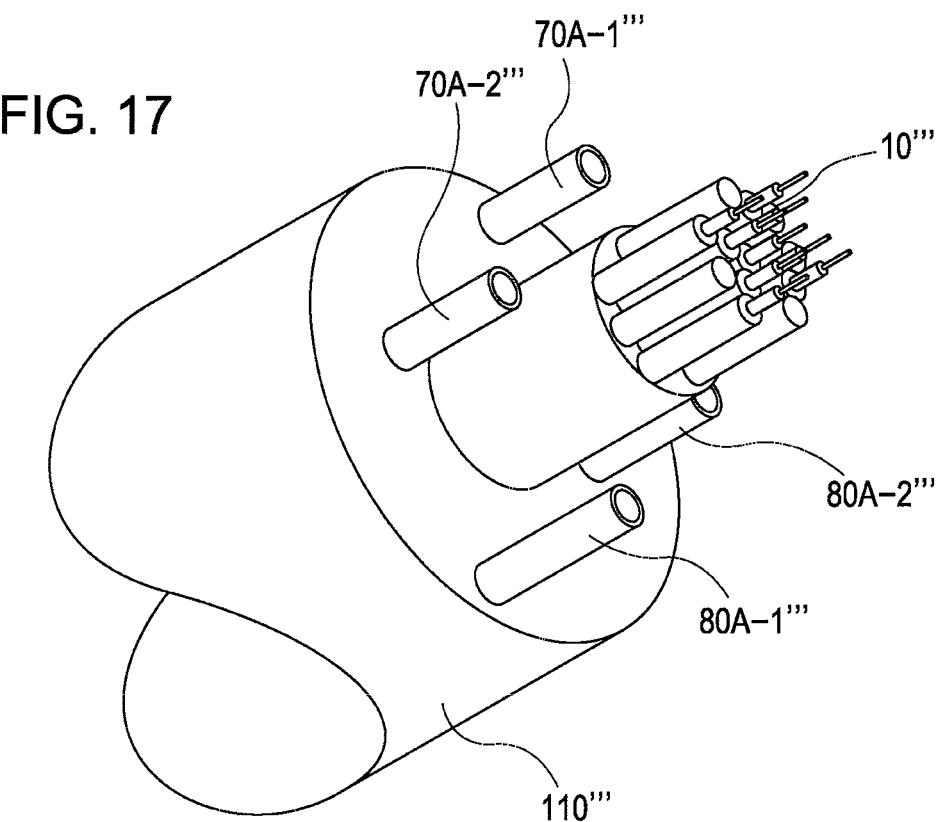
FIG. 17 is an expanded perspective view illustrating a portion of the transducer cable as shown in the fourth embodiment of the probe according to the current invention.

Now referring to FIG. 17, a drawing in an expanded perspective view illustrates a portion of the transducer cable 110''' as shown in the fourth embodiment of the probe 400 according to the current invention. The rear portion of the probe 400 includes the two sets of intake and exhaust ports 70A-1''', 80A-1''', 70A-2''' and 80A-2''', which surround the signal coax 10'''. The intake and exhaust ports 70A-1''' and 80A-1''' are located farther away from the signal coax 10''' than the intake and exhaust ports 70A-2''' and 80A-2''' as will be later explained in detail.

Figure 18:
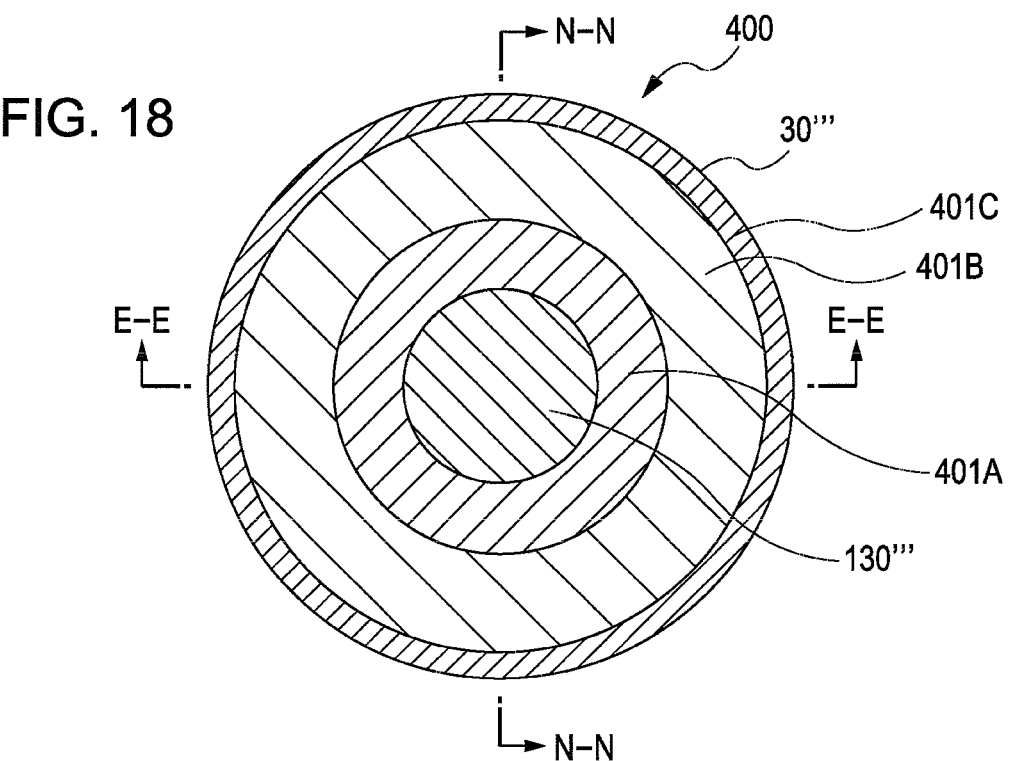
FIG. 18 is a frontal view of the probe in the fourth embodiment according to the current invention.

FIG. 18 is a frontal view of the probe 400 in the fourth embodiment according to the current invention. The front end portion of the probe 400 has four concentric areas including the most inner area which coincides with the lens 130''', a surrounding area 401A, a first slanted area 401B and a second slanted area 401C. In further detail, the surrounding area 401A, the first slanted area 401B and the second slanted area 401C are also a part of the housing portion 401 of the probe 400 and form the outer wall 30'''. The frontal view also indicates two planes N-N and E-E, which are perpendicular to each other and will be later described with respect to transverse cross sectional views in FIGS. 19 and 21.

Figure 19:
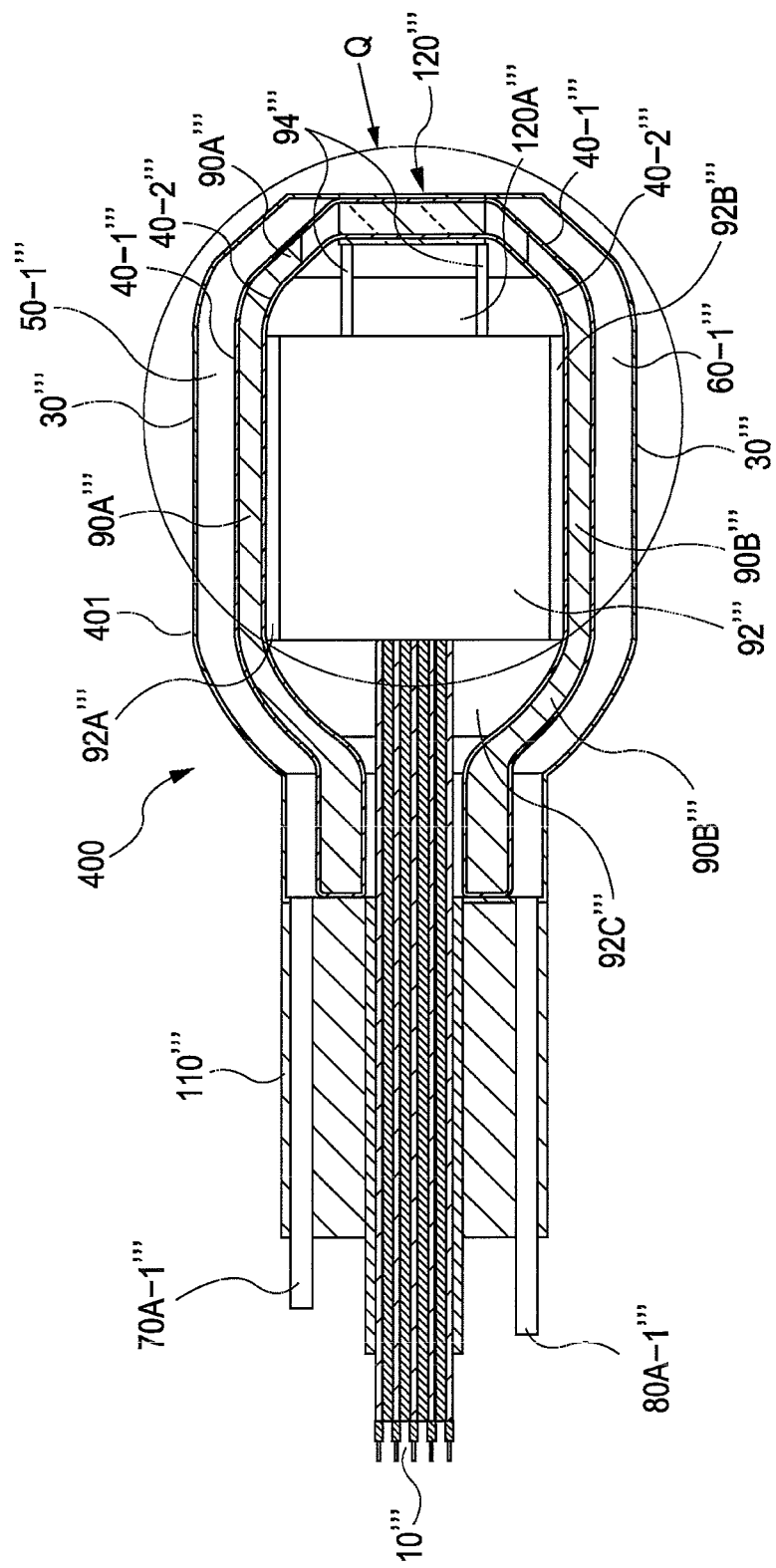
FIG. 19 is a drawing illustrating the fourth embodiment of the probe according to the current invention in a longitudinal cross sectional view on a predetermined plane N-N of FIG. 18.

Now referring to FIG. 19, a drawing illustrates the fourth embodiment of the probe 400 according to the current invention in a longitudinal cross sectional view on a predetermined plane N-N of FIG. 18. The longitudinal cross sectional view illustrates that the probe 400 includes the housing portion 401, the transducer cable 110''' at one end and the array 120''' at the other end. The housing portion 401 houses electronic units 92''', and the signal coax 10''' extends to the electronic units 92''' in the transducer cable 110'''. A ribbon of flexible cables 94''' connects the electronic units 92''' to the array 120'''. As already described above, a majority of the housing portion 401 overlaps the outer jacket or outer wall 30''' of the probe 400, and the outer jacket or outer wall 30''' extends from a point near the array 120''' to a point where the housing portion 401 meets the transducer cable 110'''. A first inner jacket or inner wall 40-1''' is located inside the outer wall 30''' and between the electronic units 92''' and the outer wall 30'''. A second inner jacket or inner wall 40-2''' is also located inside the outer wall 30''' and between the electronic units 92''' and the first inner jacket or inner wall 40-1'''. Both of the first and second inner jackets or inner walls 40-1''' and 40-2''' also extend in a longitudinal direction from a point near the array 120''' to a point where the housing portion 401 meets the transducer cable 110'''.

The first inner wall 40-1''' and the outer wall 30''' together form a first cavity or a first medium flow space 50-1''' and 60-1''' where a predetermined heat-carrying medium such as any combination of gas and or liquid materials is contained in order to transfer the undesirable or wasteful heat generated from the electronic units 92''' and or the arrays 120'''. By the same token, the first inner wall 40-1''' and the second inner wall 40-2''' also together form a second cavity or a second medium flow space where a predetermined heat-carrying medium such as any combination of gas and or liquid materials is contained in order to transfer the undesirable or wasteful heat generated from the electronic units 92''' and or the arrays 120'''. However, the longitudinal cross sectional view on the plane N-N in FIG. 19 fails to show the second medium flow space since dividing walls 90A''' and 90B''' are located over the second medium flow space.

The dividing walls 90A''' and 90B''' are each connected to both the first inner wall 40-1''' and the second inner wall 40-2''' and separate the second medium flow space into at least two halves where the predetermined heat-carrying medium such as any combination of gas and or liquid materials is contained in order to transfer the undesirable or wasteful heat generated from the electronic units 92''' and or the arrays 120'''. The dividing walls 90A''' and 90B''' also substantially extend in a longitudinal direction from a point near the array 120''' to a point where the housing portion 401 meets the transducer cable 110''' as will be further explained with respect to FIG. 20. Since the second medium flow space substantially extend in the longitudinal direction of the probe 400, each of the divided second medium flow spaces also extends to substantially the same extent in the longitudinal direction.

Figure 20:
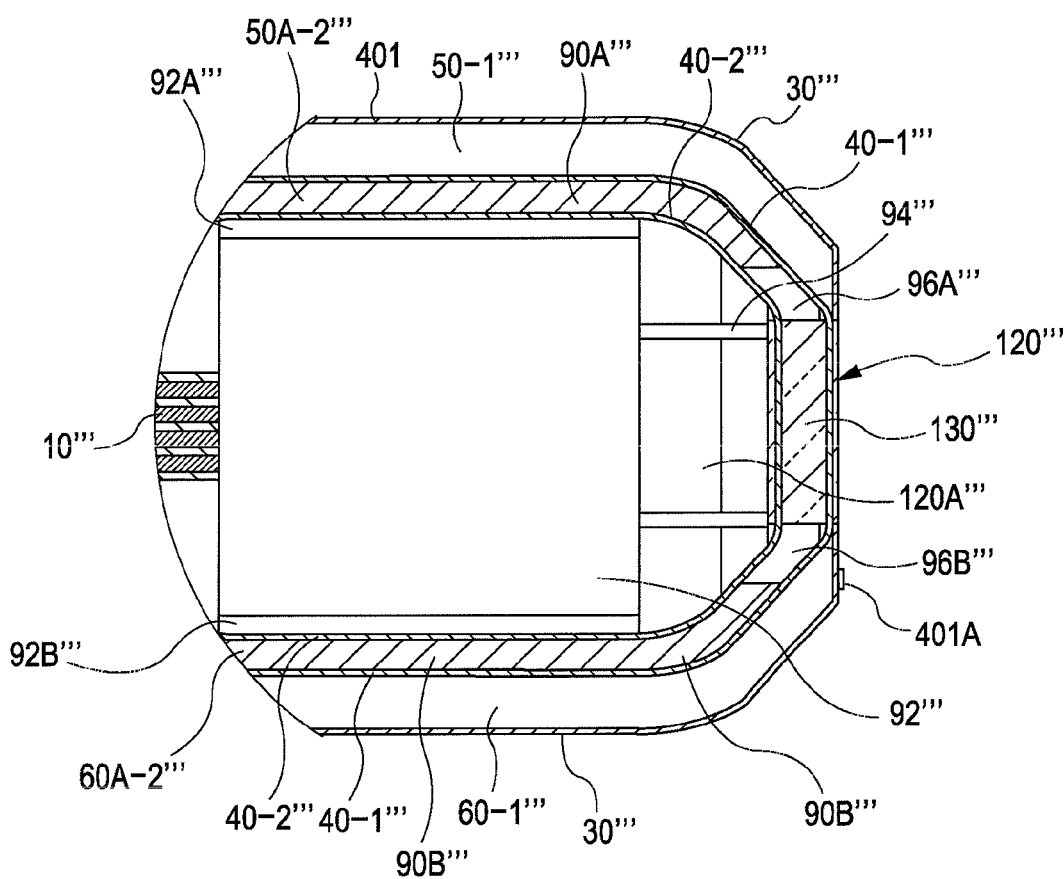
FIG. 20 is an enlarged cross sectional view illustrating the fourth embodiment in the region Q of FIG. 19.

Now referring to FIG. 20, an enlarged cross sectional view illustrates further details of the fourth embodiment in a region Q of FIG. 19. The expanded cross sectional view of the region Q shows that the first inner wall 40-1''' and the outer wall 30''' together form the first medium flow spaces 50-1''' and 60-1''', which extend beyond the electronic units 92''' and both ends of the first medium flow spaces 50-1''' and 60-1''' taper off before abutting the side surface of the array unit 120''' at the anterior end of the probe 400. The frontal end of the probe 400 forms a flat surface with the surrounding area 401A along with the array 120'''. The array unit 120''' is covered by a lens 130''' over its front end surface and is connected to the electronic units 92''' via the flexible cables 94''' at the rear end.

On the other hand, the dividing walls 90A''' and 90B''' also extend beyond the electronic unit 92''' but stop before abutting on the side surface of the array unit 120''' at the anterior end of the probe 400. By this way, the dividing walls 90A''' and 90B''' respectively form pass through openings 96A''' and 96B''' near the array unit 120'''. The pass through openings 96A''' and 96B''' each provide a connection passage between the second intake volume 50A-2''' and the second exhaust volume 60A-2''' in the second medium flow spaces. The connected intake and exhaust volume 50A-2''' and 60A-2''' together form a second continuous medium flow path for the predetermined medium to circulate as the predetermined medium absorbs the wasteful heat from the electronic units 92''' and or the array unit 120'''. The flow in the continuous medium flow path is not necessarily in a single direction to practice the claimed invention. Furthermore, the number, size and location of the pass through openings 96A''' and 96B''' are optionally modified in alternative embodiments to practice the claimed invention. The continuous medium flow path is either open or closed to the environment. In addition, the circulation or flow is optionally promoted by an external device that is connected to the ports and in alternative embodiments.

Figure 21:
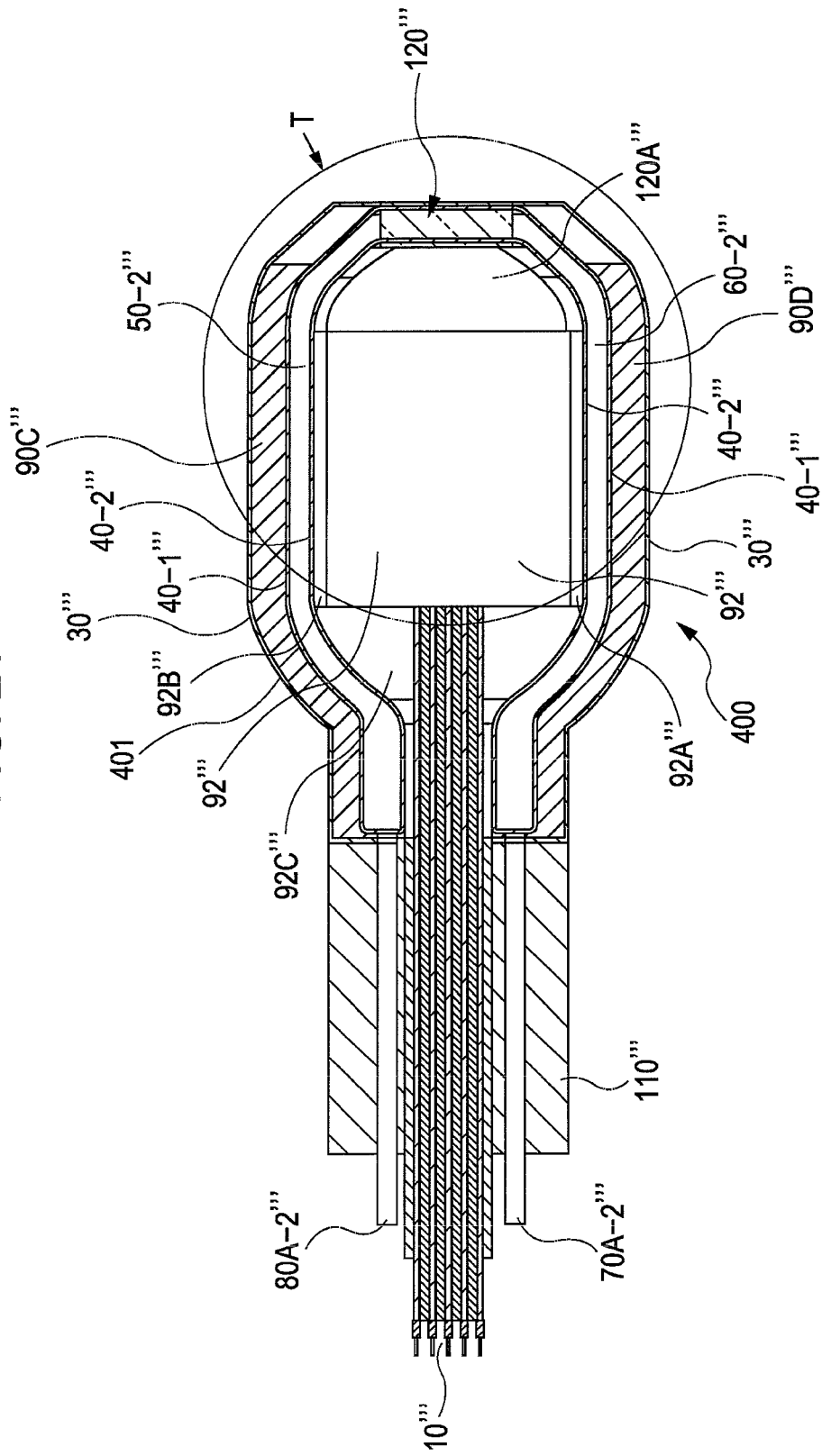
FIG. 21 is a drawing illustrating the fourth embodiment of the probe according to the current invention in a longitudinal cross sectional view on a predetermined plane E-E of FIG. 18.

Now referring to FIG. 21, a drawing illustrates the fourth embodiment of the probe 400 according to the current invention in a longitudinal cross sectional view on a predetermined plane E-E of FIG. 18. The longitudinal cross sectional view of FIG. 21 is perpendicular to the longitudinal cross sectional view of FIG. 19. The longitudinal cross sectional view illustrates that the probe 400 includes the housing portion 401, the transducer cable 110''' at one end and the array 120''' at the other end. The housing portion 401 houses electronic units 92''', and the signal coax 10''' extends to the electronic units 92''' in the transducer cable 110'''. As already described above, a majority of the housing portion 401 overlaps the outer jacket or outer wall 30''' of the probe 400, and the outer jacket or outer wall 30''' extends from a point near the array 120''' to a point where the housing portion 401 meets the transducer cable 110'''. A first inner jacket or inner wall 40-1''' is located inside the outer wall 30''' and between the electronic units 92''' and the outer wall 30'''. A second inner jacket or inner wall 40-2''' is also located inside the outer wall 30''' and between the electronic units 92''' and the first inner jacket or inner wall 40-1'''. Both of the first and second inner jackets or inner walls 40-1''' and 40-2''' also extend in a longitudinal direction from a point near the array 120''' to a point where the housing portion 401 meets the transducer cable 110'''.

The first inner wall 40-1''' and the outer wall 30''' together form a first cavity or a first medium flow space where a predetermined heat-carrying medium such as any combination of gas and or liquid materials is contained in order to transfer the undesirable or wasteful heat generated from the electronic units 92''' and or the arrays 120'''. By the same token, the first inner wall 40-1''' and the second inner wall 40-2''' also together form a second cavity or a second medium flow space 50-2''' and 60-2''' where a predetermined heat-carrying medium such as any combination of gas and or liquid materials is contained in order to transfer the undesirable or wasteful heat generated from the electronic units 92''' and or the arrays 120'''. However, the longitudinal cross sectional view on the plane E-E in FIG. 21 fails to show the first medium flow space since dividing walls 90C''' and 90D''' are located over the first medium flow space.

Figure 22:
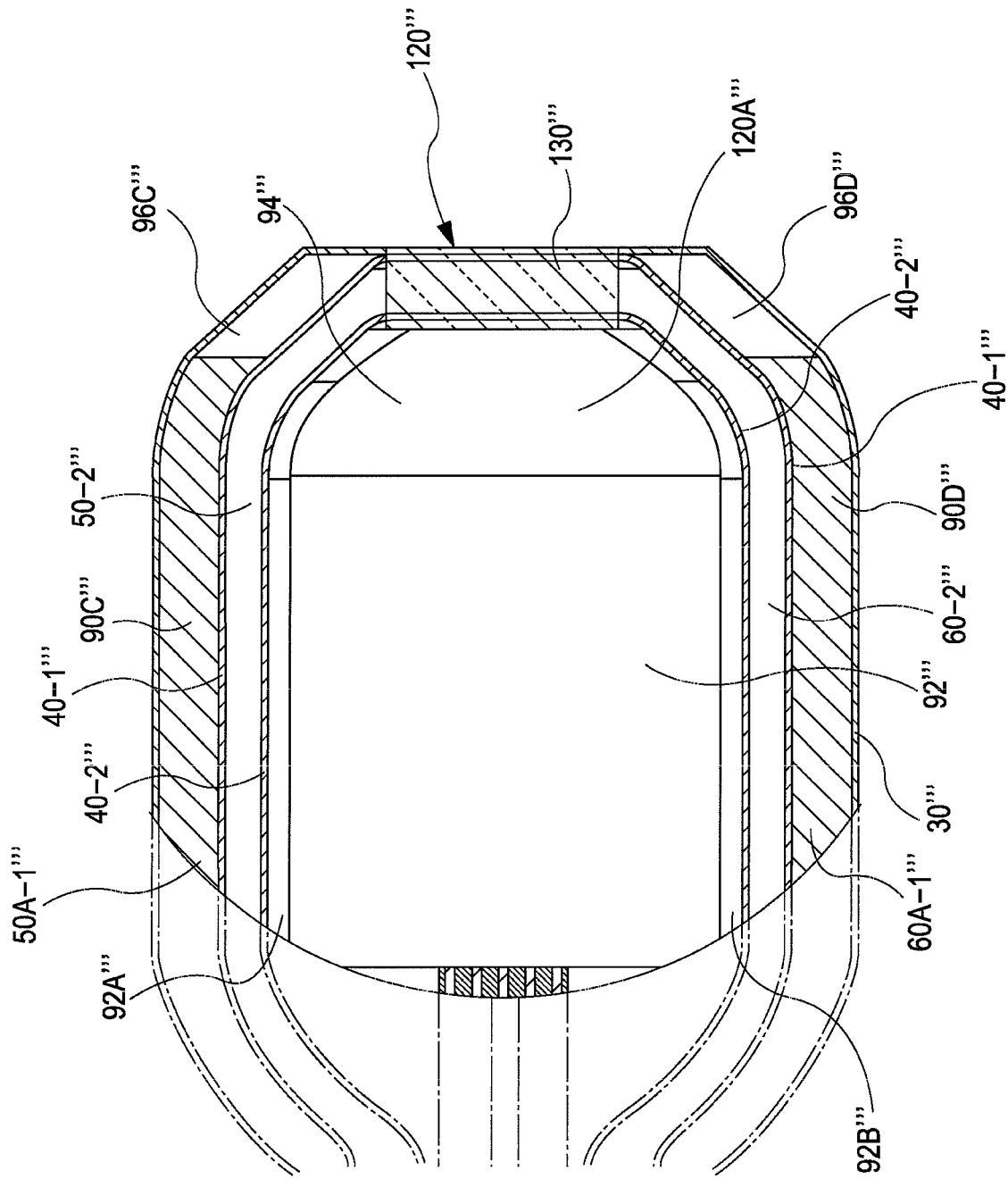
FIG. 22 is an enlarged cross sectional view illustrating the fourth embodiment in a region T of FIG. 21.

The dividing walls 90C''' and 90D''' are each connected to both the first inner wall 40-1''' and the outer wall 30''' and separate the first medium flow space into at least two halves where the predetermined heat-carrying medium such as any combination of gas and or liquid materials is contained in order to transfer the undesirable or wasteful heat generated from the electronic units 92''' and or the arrays 120''' The dividing walls 90C''' and 90D''' also substantially extend in a longitudinal direction from a point near the array 120''' to a point where the housing portion 401 meets the transducer cable 110''' as will be further explained with respect to FIG. 22. Since the first medium flow space substantially extend in the longitudinal direction of the probe 400, each of the divided first medium flow spaces also extends to substantially the same extent in the longitudinal direction.

Now referring to FIG. 22, an enlarged cross sectional view illustrates further details of the fourth embodiment in a region T of FIG. 21. The expanded cross sectional view of the region T shows that the first inner wall 40-1''' and the second inner wall 40-2''' together form the second medium flow spaces 50-2''' and 60-2''', which extend beyond the electronic units 92''' and both ends of the second medium flow spaces 50-2''' and 60-2''' abut the side surface of the array unit 120''' at the anterior end of the probe 400. The array unit 120''' is covered by a lens 130''' over its front end surface. On the other hand, the dividing wails 90C''' and 90D''' also extend beyond the electronic unit 92''' but stop before abutting on the side surface of the array unit 120''' at the anterior end of the probe 400. By this way, the dividing walls 90C''' and 90D''' respectively form pass through openings 96C''' and 96D''' near the array unit 120'''. The pass through openings 96C''' and 96D''' provide a connection passage between the first intake volume 50A-1''' and the first exhaust volume 60A-1''' in the first medium flow spaces. The connected intake and exhaust volume 50A-1''' and 60A-1''' together form a first continuous medium flow path for the predetermined medium to circulate as the predetermined medium absorbs the wasteful heat from the electronic units 92''' and or the array unit 120'''. The flow in the continuous medium flow path is not necessarily in a single direction to practice the claimed invention. Furthermore, the number, size and location of the pass through openings 96C''' and 96D''' are optionally modified in alternative embodiments to practice the claimed invention. The continuous medium flow path is either open or closed to the environment. In addition, the circulation or flow is optionally promoted by an external device that is connected to the ports and in alternative embodiments.

Referring generally to FIGS. 19, 20, 21 and 22, the undesirable heat travels towards the outer wall 30''' from the electronic units 92''' and or the array unit 120''' mostly through the first and second inner walls 40-1''' and 40-2'''. In this regard, the first and second inner walls 40-1''' and 40-2''' are made of material whose heat conductive characteristic is at least higher than that of the outer wall 30''' so that the wasteful heat easily conducts to the predetermined heat-carrying medium but not to the outer surfaces of the outer wall 30''', which may be made of a heat resistant material. For example, in one embodiment, the first and second inner walls 40-1''' and 40-2''' are made of a heat conductive material such as plastics, aluminum, carbon/aluminum, copper, graphite, any other well-known heat-conductive material or a combination of the above. In further detail, the first and second inner walls 40-1''' and 40-2''' are optionally made of the same material or a different material. By the same token, the predetermined heat-carrying medium is optionally the same medium or a different medium in the first and second medium flow spaces 50-1''', 60-1''', 50-2''' and 60-2'''.

Still referring generally to FIGS. 19, 20, 21 and 22, a heat removing mechanism surrounds a substantial portion of the heat generating sources such as the electronic units 92''' and the array unit 120'''. That is, since both the first and second medium flow spaces 50-1''', 60-1''', 50-2''' and 60-2''' substantially extend in a longitudinal direction of the probe 400 and contain the predetermined heat-carrying medium, a substantial amount of the undesirable heat from the electronic units 92''' and or the arrays 120''' is absorbed by predetermined heat-carrying medium in the first and second medium flow spaces 50-1''', 60-1''', 50-2''' and 60-2''' before reaching the outer wall 30'''. In one exemplary embodiment of the probe 400, the heat-carrying medium travels substantially in one direction from an intake inlet 70A-1''' through the first medium flow space 50-1''' to an exhaust outlet 80A-1''' through the first medium flow space 60-1'''. The above described medium flow movement is not necessary to practice the current invention and can be implemented in different directions or manners.

In the embodiment as shown in FIGS. 19, 20, 21 and 22, only two layers of the first and second medium flow spaces 50-1''', 60-1''', 50-2''' and 60-2''' are described. The current invention is not limited to the two medium flow spaces as explicitly claimed in the claim. In this regard, any number of medium flow spaces is optionally layered to form a multi-layered integrated cooling structure with the dividing walls in other embodiments.

These multiply layered medium flow spaces are optionally channeled into a plurality of independent continuous medium flow paths in certain embodiments. Alternatively, these multiply layered medium flow spaces are optionally connected into a single continuous medium flow path within the same probe in other embodiments. Furthermore, in yet other embodiments, a part of these multiply layered medium flow spaces is optionally channeled into a plurality of independent continuous medium flow paths while the rest of these multiply layered medium flow spaces is optionally connected into a single continuous medium flow path within the same probe.

Figure 23:
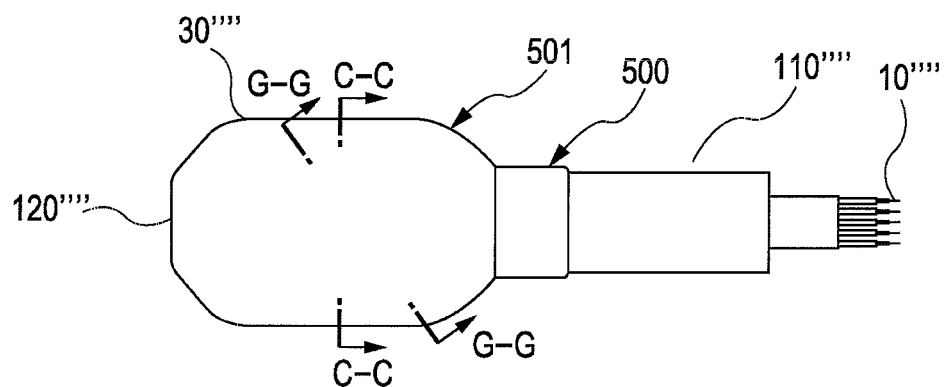
FIG. 23 is a side view of a fifth embodiment of the probe according to the current invention.

FIG. 23 is a side view of a fifth embodiment of the probe according to the current invention. A probe 500 generally includes a hand holding portion or a housing portion 501 that is attached to a transducer cable 110'''' at one end while an array of transducer elements 120'''' is located at the other end. The transducer cable 110'''' is ultimately connected to a processing unit or a system for transmitting electrical signals via signal coax 10'''' to and from the probe 500. The housing portion 501 contains electronic units or components such as electronic circuits and also provides an operator with a handle area for holding the probe 500 in order to place the array 120'''' of the probe 500 over a desired area of a patient. As already described with respect to previously disclosed embodiments, a majority of the housing portion 501 also overlaps an outer jacket or outer wall 30'''' of the probe 500. Although this embodiment of the probe 500 is illustrated as a hand-held device that is cabled to the system, the claimed invention is not necessary limited by these requirements.

Figure 24:
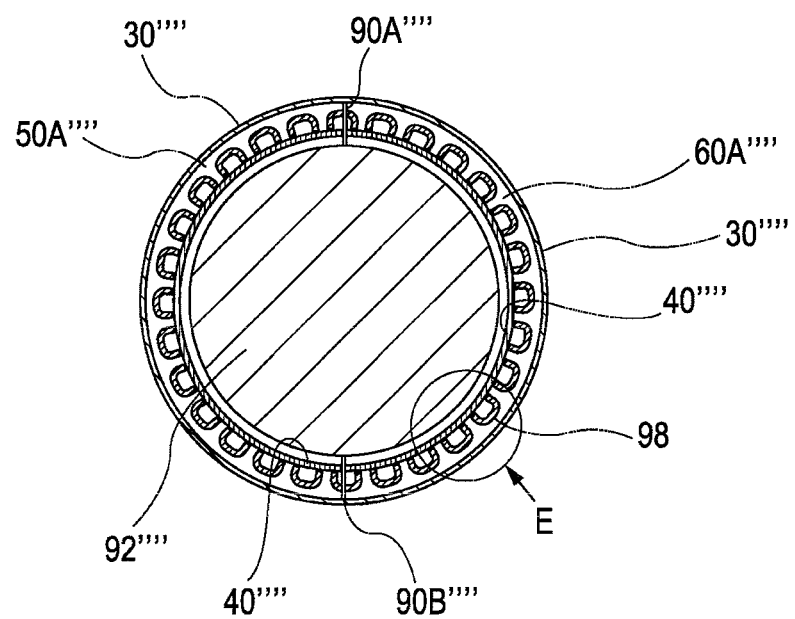
FIG. 24 is a diagram illustrating of the fifth embodiment of the probe in a transverse cross sectional view at a predetermined plane C-C of FIG. 23.

FIG. 24 is a diagram illustrating the fifth embodiment of the probe in a transverse cross sectional view at a predetermined plane C-C of FIG. 23. Both the outer wall 30'''' and the inner wall 40"" substantially surround the heat-generating electronic units 92"". The dividing walls 90A"" and 90B"" are each located between the outer wall 30"" and the inner wall 40"" and also each connected to both the outer wall 30"" and the inner wall 40"". Thus, the dividing walls 90A"" and 90B"" separate the medium flow space into an intake volume 50A"" and an exhaust volume 60A"". The transverse cross sectional view also illustrates fins 98, which are located throughout the intake volume 50A"" and the exhaust volume 60A"". For example, the inner wall 40"" is made of a heat conductive material such as plastics, aluminum, carbon/aluminum, copper, graphite, any other well-known heat-conductive material or a combination of the above. The terms, intake and exhaust do not necessarily dictate a direction of the medium flow movement, which is not necessary to practice the current invention and can be implemented in different directions or manners.

Figure 25:
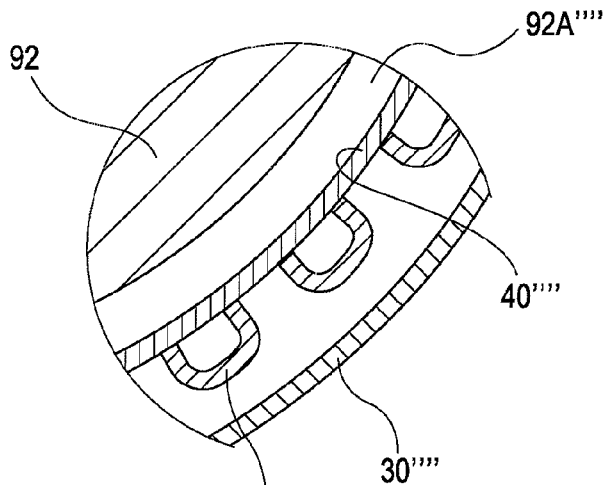
FIG. 25 in an enlarged cross sectional view illustrating the fifth embodiment of the probe in the region E of FIG. 24.

Now referring to FIG. 25, an enlarged cross sectional view illustrates the fifth embodiment of the probe 500 in the region E of FIG. 24. The fins 98 are located between the outer wall 30"" and the inner wall 40"" and on the surface of the inner walls 40"" facing the outer wall 30"". The fins 98 substantially increase the surface area for improving the power dissipation. In one embodiment, the fins 98 are formed on the inner wall 40"" by injection molding if the inner wall 40"" is made of plastic. In another embodiment, if the inner wall 40"" is made of metal or some other material, the fins 98 is optionally formed by using other means like skiving, injection molding or a wire EDM process. A number, shape and size of the fins 98 is not limited to any particular requirement or range.

Figure 26:
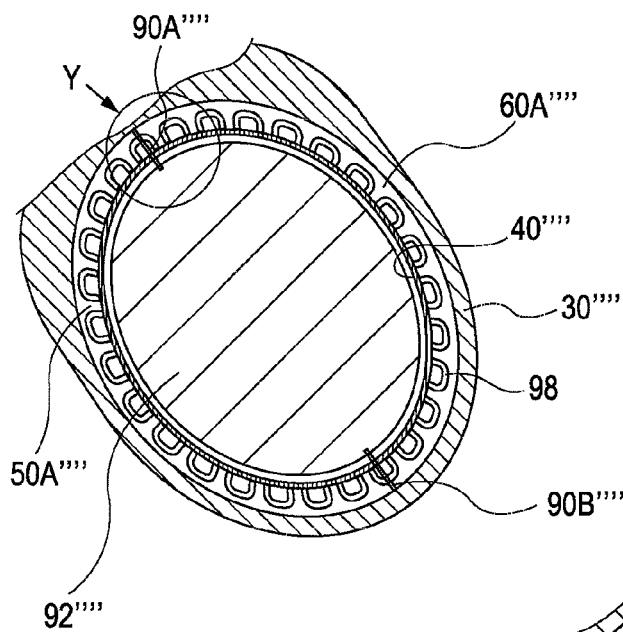
FIG. 26 is a diagram illustrating of the fifth embodiment of the probe in an oblique cross sectional view at a predetermined plane G-G of FIG. 23.

FIG. 26 is a diagram illustrating of the fifth embodiment of the probe in an oblique cross sectional view at a predetermined plane G-G of FIG. 23. Both the outer wall 30"" and the inner wall 40"" substantially surround the heat-generating electronic units 92"". The dividing walls 90A"" and 90B"" are each located between the outer wall 30"" and the inner wall 40"" and also each connected to both the outer wall 30"" and the inner wall 40"". Thus, the dividing walls 90A"" and 90B"" separate the medium flow space into an intake volume 50A"" and an exhaust volume 60A"". The oblique cross sectional view also illustrates fins 98, which are located throughout the intake volume 50A"" and the exhaust volume 60A"".

Figure 27:
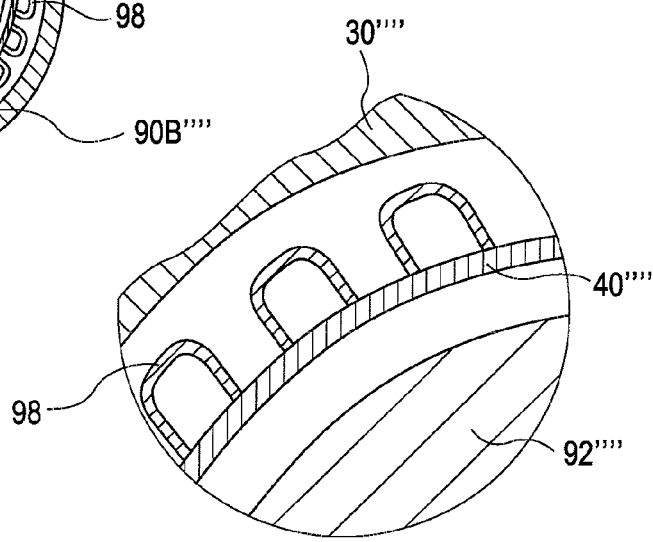
FIG. 27 is an enlarged cross sectional view illustrating the fifth embodiment of the probe in the region J of FIG. 26.

Now referring to FIG. 27, an enlarged cross sectional view illustrates the fifth embodiment of the probe 500 in the region J of FIG. 26. The fins 98 are located between the outer wall 30"" and the inner wall 40"" and on the surface of the inner walls 40"" facing the outer wall 30"". The fins 98 substantially increase the surface area for improving the power dissipation. The enlarged oblique cross sectional view shows that the fins 98 are also elongated and U-shaped. A number, shape and size of the fins 98 is not limited to any particular requirement or range.

The above described fins 98 are optionally incorporated into any of the first through fourth embodiments as illustrated in FIGS. 1A through 22. In addition, in the fourth embodiment, the fins 98 are incorporated on all or any number of the inner wails in the medium flow paths.

Figure 28:
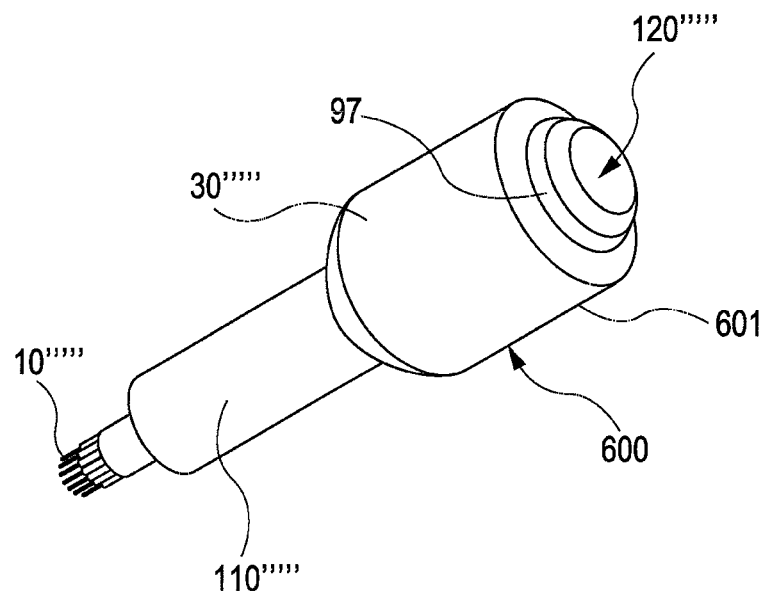
FIG. 28 is a perspective view illustrating a sixth embodiment of the probe according to the current invention.

Now referring to FIG. 28, a perspective view illustrates a sixth embodiment of the probe according to the current invention. A probe 600 generally includes a hand holding portion or a housing portion 601 that is attached to a transducer cable 110"" at one end while an array of transducer elements 120"" is located at the other end. The transducer cable 110"" is ultimately connected to a processing unit or a system for transmitting electrical signals via signal coax 10"" to and from the probe 600. The housing portion 601 contains electronic units or components such as electronic circuits and also provides an operator with a handle area for holding the probe 600 in order to place the array 120"" of the probe 600 over a desired area of a patient. As already described with respect to previously disclosed embodiments, a majority of the housing portion 601 also overlaps an outer jacket or outer wall 30"" of the probe 600. Although this embodiment of the probe 600 is illustrated as a hand-held device that is cabled to the system, the claimed invention is not necessary limited by these requirements.

Figure 29:
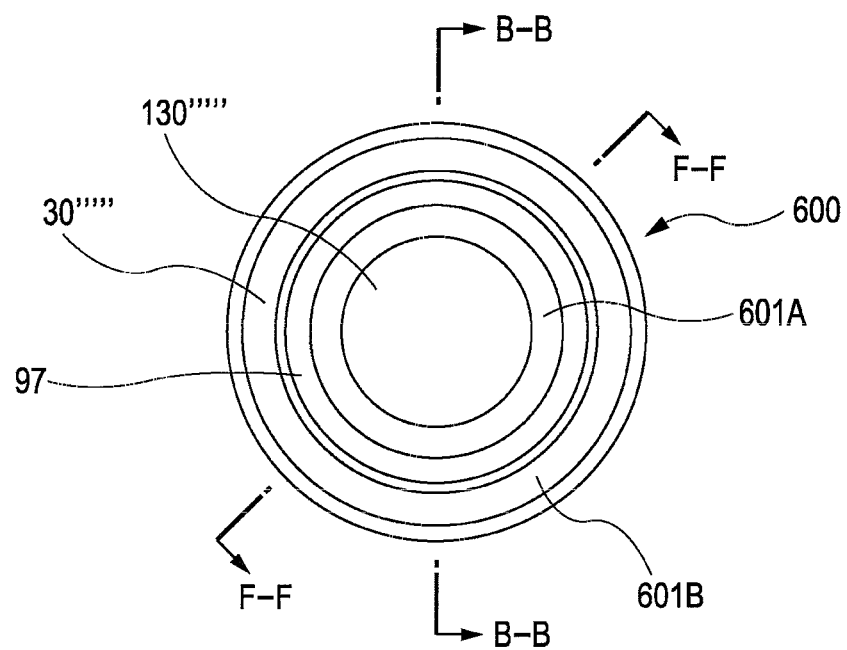
FIG. 29 is a frontal view of the probe in the sixth embodiment according to the current invention.

FIG. 29 is a frontal view of the probe 600 in the sixth embodiment according to the current invention. The front end portion of the probe 600 has four concentric areas including the most inner area which coincides with the lens 130"", a first surrounding area 601A, a vent 97 and a second surrounding area 601B. The vent 97 is provided to improve the cooling efficiency in the probe 600. In further detail, the first and surrounding area 601A and the second surrounding area 401B are also a part of the housing portion 601 of the probe 600 and form the outer wall 30"". The frontal view also indicates two planes B-B and F-F, which will be later described with respect to transverse cross sectional views in FIGS. 30 and 31.

Figure 30:
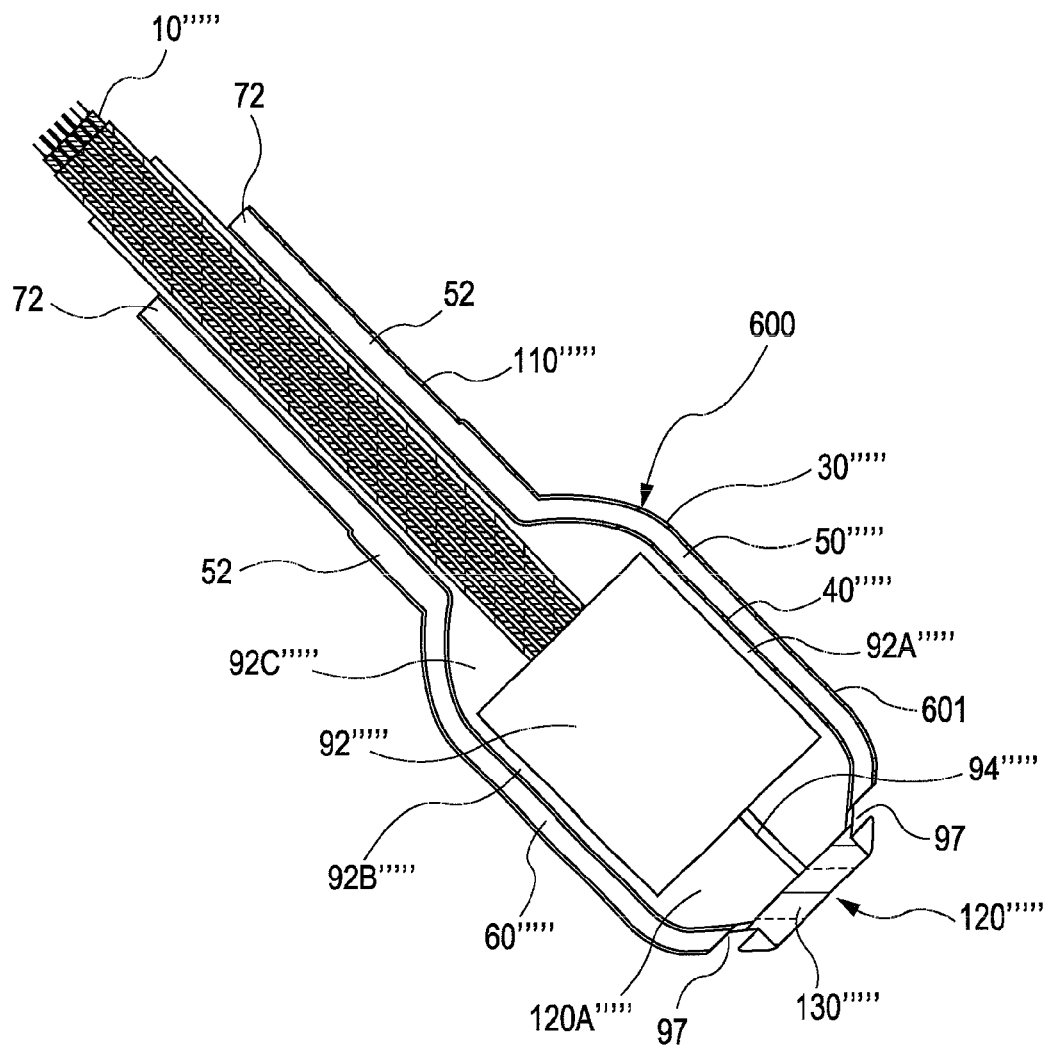
FIG. 30 is a drawing illustrating the sixth embodiment of the probe according to the current invention in a longitudinal cross sectional view on a predetermined plane F-F of FIG. 29.

Now referring to FIG. 30, a drawing illustrates the sixth embodiment of the probe 600 according to the current invention in a longitudinal cross sectional view on a predetermined plane F-F of FIG. 29. The longitudinal cross sectional view illustrates that the probe 600 includes the housing portion 601, the transducer cable 110"" at one end and the array 120"" at the other end. The housing portion 601 houses electronic units 92"", and the signal coax 10"" extends to the electronic units 92"" in the transducer cable 110"". A ribbon of a flexible cable 94"" connects the electronic units 92"" to the array 120"". A majority of the housing portion 601 overlaps the outer jacket or outer wall 30"" of the probe 600, and the outer jacket or outer wall 30"" extends from a point near the array 120"" to a point where the housing portion 601 meets the transducer cable 110"". An inner jacket or inner wall 40"" is located inside the outer wall 30"" and between the electronic units 92"" and the outer wall 30"". The inner jacket or inner wall 40"" also extends in a longitudinal direction from a point near the array 120"" to a point where the housing portion 601 meets the transducer cable 110"".

The inner wall 40"" and the outer wall 30"" together form a cavity or a medium flow space 50"" and 60"" where a predetermined heat-carrying medium such as any combination of solid, gas and or liquid materials is contained in order to transfer the undesirable or wasteful heat generated from the electronic units 92"" and or the arrays 120"". A phase change in the heat-carrying medium is optionally used for heat transfer. In general, the undesirable heat travels towards the outer wall 30"" through the inner wall 40"". In this regard, the inner wall 40"" is made of material whose heat conductive characteristic is at least higher than that of the outer wall 30"" so that the wasteful heat easily conducts to the predetermined heat-carrying medium but not to the outer surfaces of the outer wall 30"". For example, the inner wall 40"" is made of a heat conductive material such as plastics, aluminum, carbon/aluminum, copper, graphite, any other well-known heat-conductive material or a combination of the above. Since the medium flow space 50"" and 60"" substantially extend in a longitudinal direction of the probe 600 and contain the predetermined heat-carrying medium, a substantial amount of the undesirable heat from the electronic units 92"" and or the arrays 120"" is absorbed by predetermined heat-carrying medium before reaching the outer wall 30"". In one exemplary embodiment of the probe 600, the heat-carrying medium travels substantially in one direction from an intake/exhaust opening 72 through the intake/exhaust volume .52, some of the absorbed heat escapes to the environment through the vent 97. The above described medium flow movement is not necessary to practice the current invention and can be implemented in different directions or manners.

Figure 31:
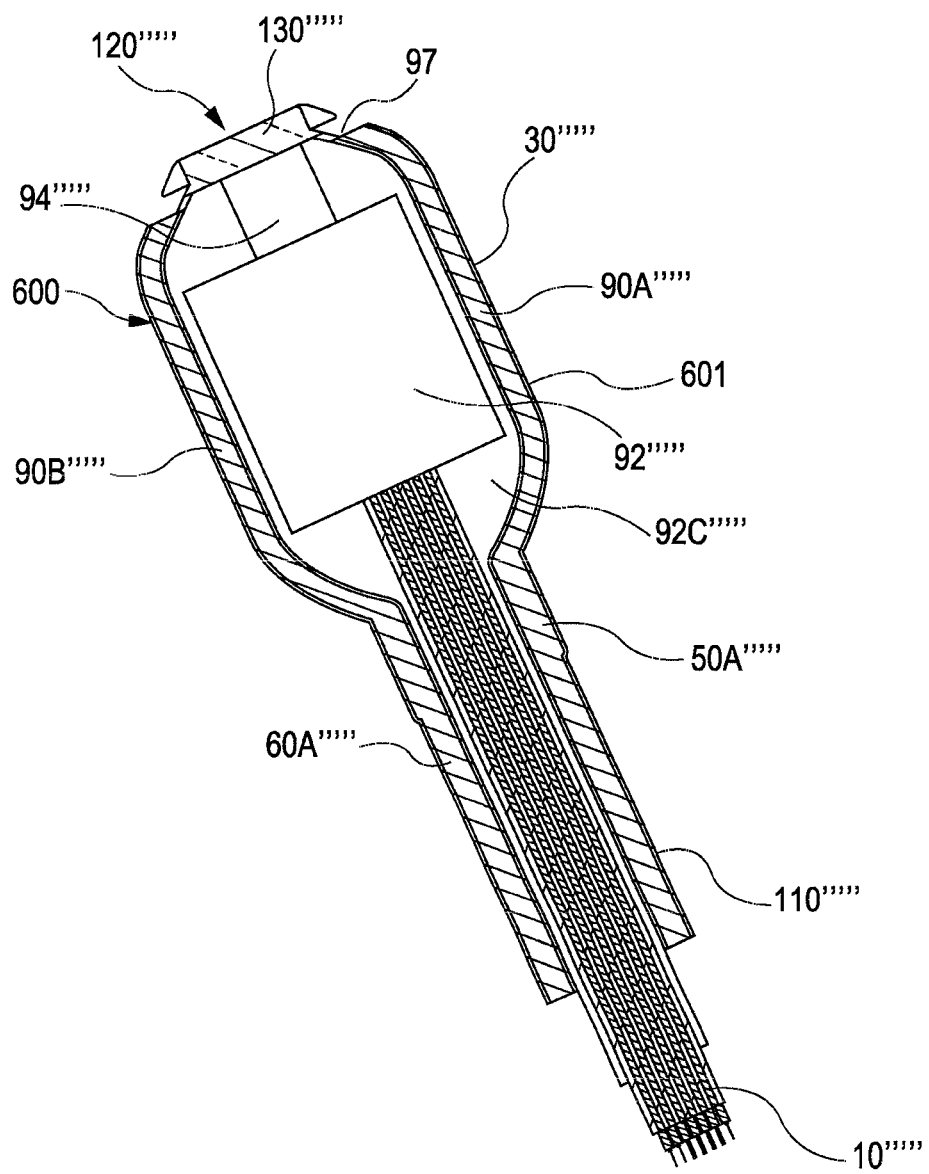
FIG. 31 is a drawing illustrating the sixth embodiment of the probe in a longitudinal cross sectional view on a predetermined plane B-B of FIG. 29.
Figure 32:
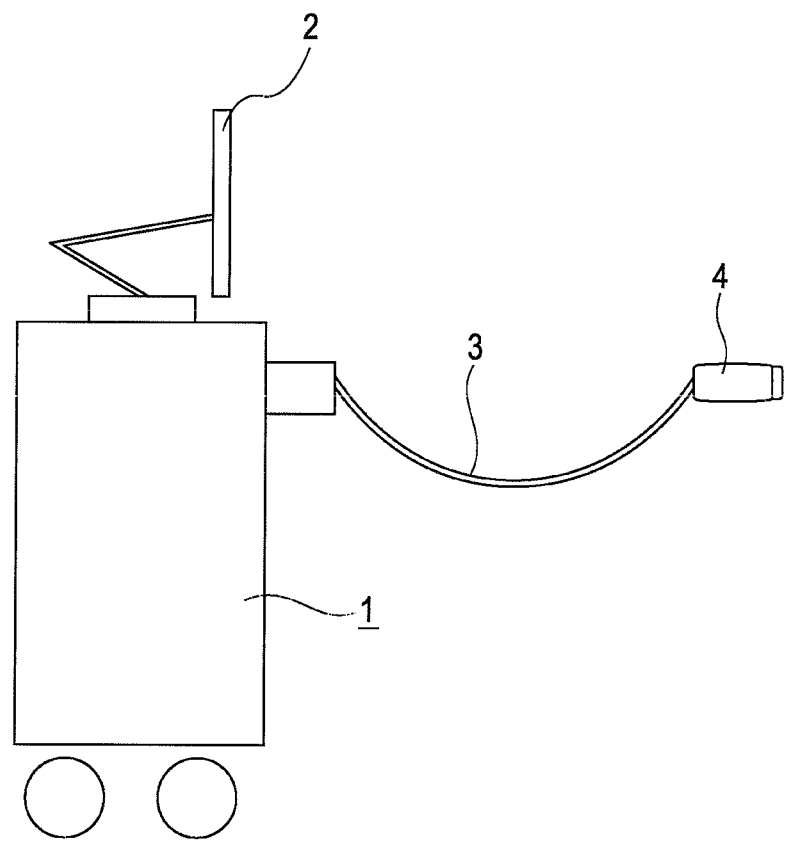
FIG. 32 is a diagram illustrating one exemplary prior art ultrasound imaging system.

Now referring to FIG. 31, a drawing illustrates the sixth embodiment of the probe 600 in a longitudinal cross sectional view on a predetermined plane B-B of FIG. 29. FIG. 31 illustrates that the housing portion 601 houses electronic units 92'''', and the signal coax 10'''' is connected to the electronic units 92''''. A ribbon of the flexible cable 94'''' connects the electronic units 92'''' to the array 120''''. The longitudinal cross sectional view of FIG. 31 does not show the separation of the inner wall 40'''' and the outer wall 30'''' due to dividing walls 90A'''' and 90B''''. However, as already described above with respect to FIG. 30, a majority of the housing portion 601 overlaps the outer wall 30'''', which extends from a point near the array 120'''' to a point where the housing portion 601 meets the transducer cable 110''''. As also already described above, the inner wall 40'''' is located inside the outer wall 30'''' and between the electronic units 92'''' and the outer wall 30''''. The inner wall 40'''' also extends in a longitudinal direction from a point near the array 120'''' to a point where the housing portion 601 meets the transducer cable 110''''. The dividing walls 90A'''' and 90B'''' are fainted between the outer wall 30'''' and the inner wall 40'''' on the predetermined plane B-B along the longitudinal direction.

The dividing walls 90A'''' and 90B'''' are each connected to both the inner wall 40'''' and the outer wall 30'''' and separate the medium flow space 50'''' and 60'''' into at least two halves where the predetermined heat-carrying medium such as any combination of solid, gas and or liquid materials is contained in order to transfer the undesirable or wasteful heat generated from the electronic units 92'''' and or the arrays 120''''. The dividing walls 90A'''' and 90B'''' also substantially extend in the longitudinal direction from a point near the array 120'''' to a point where the housing portion 601 meets the transducer cable 110''''. Since the medium flow space 50'''' and 60'''' substantially extend in the longitudinal direction of the probe 600, each of the divided medium flow spaces 50'''' and 60'''' also extends to substantially the same extent in the longitudinal direction.

Still referring to FIG. 31, the dividing walls 90A'''' and 90B'''' extend beyond the electronic unit 92'''' but stop before reaching the array unit 120'''' at the anterior end of the probe 600. By this way, the vent 97, the inner wall 40'''' and the outer wall 30'''' together form an open common pass through volume near and in front of the array unit 120''''. The connected intake and exhaust volume 50A'''' and 60A'''' together form a continuous medium flow path for the predetermined medium to circulate as the predetermined medium absorbs the wasteful heat from the electronic units 92'' and or the array unit 120''. The open pass through volume provides a connection passage between the medium flow spaces 50'''' and 60'''' for some of the absorbed heat to escape to the environment through the vent 97.

The vent 97 is optionally implemented in various manners and shapes. For example, the vent 97 is either sealed or open to the environment. If a heat-carrying medium is air, the vent 97 is optionally open as described above. On the other hand, if a heat-carrying medium is gas other than air, liquid or any other combined material, a continuous medium flow path is closed so that the predetermined medium is not directly released to the environment, and the vent 97 is optionally sealed from the environment for containing the heat-carrying medium within the probe 600. In one alternative embodiment, the sealed vent is a heat transfer area or a heat sink located on the outer wall where the patient or the user makes no contact. The sealed vent on the outer wall provides an additional heat releasing mechanism for the probe. Furthermore, the vent 97 is implemented to have various sizes, shapes and locations depending upon applications and functional priorities of a particular probe design.

The above described vents 97 of the sixth embodiment are optionally incorporated into any of the first through fifth embodiments of FIGS. 1A through 27. In certain embodiments featuring a multi-layered cooling structure as illustrated in FIGS. 16 through 22, the vents 97 are optionally placed only on the outer walls. In other embodiments featuring a multi-layered cooling structure, the vents 97 are optionally placed on any number of the inner walls. Of course, the vents 97 are also optionally placed on both the inner walls and the outer wall in alternative embodiments.

For additional detail of the first through sixth embodiments of the probe as illustrated in FIGS. 1A through 31, certain heat conducting mechanisms/techniques are optionally applied to promote the heat conductance between the undesirable heat generating elements and the above described integrally formed cooling structure of the probe. As described with respect to the first through sixth embodiments of the probe, since the heating generating elements such as the electronic elements and the array are surrounded by interstitial spaces with in the probe housing, the efficient heat conductance in the interstitial spaces substantially improves the heat removing efficiency in the probe. In other words, a heat coupling structure improves heat coupling in the interstitial spaces between the integrally formed cooling structure and the heat generating elements. The heat coupling structure includes any combination of heat pipes, thermal electric cooler (TEC), direct contact with thermal compound, heat spreaders such as copper, aluminum, carbon/aluminum, phase change material and or a thermally conductive liquid. Of course, the heat generating elements should be electrically isolated if they are submerged in the thermally conductive liquid. For example, these improved heat coupling mechanisms are optionally placed in one embodiment in the interstitial spaces 92A, 92B, 92C surrounding electronics and an interstitial space 120A behind the array 120 as indicated in FIGS. 2B and 4B. Similarly, the interstitial spaces are indicated by the corresponding reference numerals for other embodiments in FIGS. 7B, 9B, 12B, 14, 19, 20, 24 and 30.

While certain embodiments have been described above, these embodiments have been presented by way of example only and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope of the inventions.

What is claimed is:

1. An ultrasound probe, comprising:
a plurality of heat-generating units for generating undesirable heat;
an outer wall for housing said heat-generating units;
an inner wall located between said outer wall and said heat-generating units for forming medium flow spaces to contain a predetermined medium for transferring the undesirable heat away from said heat-generating units; and
at least a dividing wall located between said outer wall and said inner wall and connected to both said outer wall and said inner wall for dividing said medium flow spaces into a continuous medium flow path.

2. The ultrasound probe according to claim 1 wherein said heat-generating units include at least one of an array of transducer elements and electronic circuits.

3. The ultrasound probe according to claim 2 wherein said continuous medium flow path is located behind some of said heat-generating units.

4. The ultrasound probe according to claim 2 wherein said continuous medium flow path is located in front of some of said heat-generating units.

5. The ultrasound probe according to claim 2 wherein said continuous medium flow path is located immediately adjacent to some of said heat-generating units.

6. The ultrasound probe according to claim 1 wherein said inner wall surrounds said heat-generating units.

7. The ultrasound probe according to claim 1 wherein said medium flow space surrounds said heat-generating units.

8. The ultrasound probe according to claim 1 wherein said continuous medium flow path is a closed path.

9. The ultrasound probe according to claim 8 wherein the medium includes any combination of liquid materials.

10. The ultrasound probe according to claim 8 wherein the medium includes air or any combination of gasses.

11. The ultrasound probe according to claim 8 wherein said outer wall forms at least a sealed vent for allowing some heat in the medium to be released to outside the probe.

12. The ultrasound probe according to claim 1 wherein said continuous medium flow path is an open path.

13. The ultrasound probe according to claim 12 wherein the medium includes air.

14. The ultrasound probe according to claim 13 wherein said outer wall forms at least an open vent for allowing the air to be exposed to outside the probe.

15. The ultrasound probe according to claim 1 wherein said dividing wall divides said medium flow spaces into said continuous medium flow path having an intake side and an exhaust side.

16. The ultrasound probe according to claim 15 further comprises an input port located on said intake side and an output port located on said exhaust side.

17. The ultrasound probe according to claim 15 further comprises a circulation unit for promoting circulation of the medium in said continuous medium flow path from said intake side to said exhaust side.

18. The ultrasound probe according to claim 1 wherein said outer wall is made of a first material while said inner wall is made of a second material that is at least higher heat conductive than the first material.

19. The ultrasound probe according to claim 1 further comprises a circulation unit for promoting circulation of the medium in said continuous medium flow path.

20. The ultrasound probe according to claim 1 further comprises fins located in said medium flow space.

21. The ultrasound probe according to claim 20 wherein said fins are located on said inner wall.

22. The ultrasound probe according to claim 1 further comprises a heat coupling structure located in an interstitial space between said inner wall and said heat-generating units.

23. An ultrasound probe, comprising:
heat-generating units for generating undesirable heat;
an outer wall for housing said heat-generating units;
more than one inner walls located between said outer wall and said heat-generating units for forming layers of medium flow spaces to contain at least one predetermined medium for transferring the undesirable heat away from said heat-generating units; and
a number of dividing walls each corresponding to a respective one of said inner walls and located between said outer wall and the nearest one of said inner walls and between said inner walls, one of said dividing walls connected to both said outer wall and said nearest inner wall while the rest of said dividing walls is connected to adjacent two of said inner walls for dividing at least one of said medium flow spaces into at least one continuous medium flow path.

24. The ultrasound probe according to claim 23 wherein said heat-generating units include at least one of an array of transducer elements and electronic circuits.

25. The ultrasound probe according to claim 24 wherein at least one of said continuous medium flow paths is located behind some of said heat-generating units.

26. The ultrasound probe according to claim 24 wherein at least one of said continuous medium flow paths is located in front of some of said heat-generating units.

27. The ultrasound probe according to claim 24 wherein at least one of said continuous medium flow paths is located immediately adjacent to some of said heat-generating units.

28. The ultrasound probe according to claim 23 wherein at least one of said inner walls surrounds said heat-generating units.

29. The ultrasound probe according to claim 23 wherein at least one of said medium flow spaces surrounds said heat-generating units.

30. The ultrasound probe according to claim 23 wherein any number of said continuous medium flow paths is a closed path.

31. The ultrasound probe according to claim 30 wherein the medium in said closed path includes any combination of liquid materials.

32. The ultrasound probe according to claim 30 wherein the medium in said closed path includes air or any combination of gasses.

33. The ultrasound probe according to claim 30 wherein said outer wall forms at least a sealed vent for allowing some heat in the medium to be released to outside the probe.

34. The ultrasound probe according to claim 23 wherein any number of said continuous medium flow paths is an open path.

35. The ultrasound probe according to claim 34 wherein the medium includes air.

36. The ultrasound probe according to claim 35 wherein said outer wall forms at least an open vent for allowing the medium to be exposed to outside the probe.

37. The ultrasound probe according to claim 23 wherein said dividing walls divide said medium flow spaces into said continuous medium flow paths each having an intake side and an exhaust side.

38. The ultrasound probe according to claim 37 further comprises an input port located on said intake side and an output port located on said exhaust side.

39. The ultrasound probe according to claim 37 further comprises a circulation unit for promoting circulation of the medium in any number of said continuous medium flow paths from said intake side to said exhaust side.

40. The ultrasound probe according to claim 23 wherein said outer wall is made of a first material while said inner walls is made of a second group of materials that is at least higher heat conductive than the first material.

41. The ultrasound probe according to claim 40 wherein the second group of the materials are the same material.

42. The ultrasound probe according to claim 40 wherein the second group of the materials are different materials.

43. The ultrasound probe according to claim 23 wherein the predetermined medium is the same in said continuous medium flow paths.

44. The ultrasound probe according to claim 23 wherein the predetermined medium is different in said continuous medium flow paths.

45. The ultrasound probe according to claim 23 further comprises a circulation unit for promoting circulation of the medium in any number of said continuous medium flow paths.

46. The ultrasound probe according to claim 23 wherein some of said continuous medium flow paths are connected with each other.

47. The ultrasound probe according to claim 23 wherein all of said continuous medium flow paths are connected with each other.

48. The ultrasound probe according to claim 23 wherein none of said continuous medium flow paths is connected with each other.

49. The ultrasound probe according to claim 23 further comprises fins located in at least one of said medium flow spaces.

50. The ultrasound probe according to claim 49 wherein said fins are located on at least one of said inner walls.

51. The ultrasound probe according to claim 23 further comprises a heat coupling structure located in an interstitial space between the most inner one of said inner walls and said heat-generating units.

52. An ultrasound probe, comprising:
   heat-generating units for generating undesirable heat including an array of transducer elements;
   an outer wall for housing said heat-generating units;
   an inner wall located between said outer wall and said heat-generating units for forming a medium flow space which covers a substantial portion of inner surfaces of the ultrasound probe to contain a predetermined medium for transferring the undesirable heat away from said heat-generating units; and
   a pair of dividing walls located between said outer wall and said inner wall and connected to both said outer wall and said inner wall for dividing said medium flow space into a single continuous medium flow path through pass through openings and a pass through volume, wherein said pass through volume is located behind said array.

* * * * *